US008318980B2

(12) United States Patent
Kluijtmans et al.

(10) Patent No.: US 8,318,980 B2
(45) Date of Patent: Nov. 27, 2012

(54) UV ABSORBING COMPOUNDS

(75) Inventors: Sebastianus Gerardus Johannes Maria Kluijtmans, Zeist (NL); Jan Bastiaan Bouwstra, Bosch en Duin (NL)

(73) Assignee: Fujifilm Manufacturing Europe B.V., Tilburg (NL)

( * ) Notice: Subject to any disclaimer, the term of this patent is extended or adjusted under 35 U.S.C. 154(b) by 308 days.

(21) Appl. No.: 12/678,698

(22) PCT Filed: Sep. 18, 2008

(86) PCT No.: PCT/NL2008/050614
§ 371 (c)(1),
(2), (4) Date: Mar. 17, 2010

(87) PCT Pub. No.: WO2009/038463
PCT Pub. Date: Mar. 26, 2009

(65) Prior Publication Data
US 2010/0209366 A1 Aug. 19, 2010

Related U.S. Application Data

(60) Provisional application No. 60/973,485, filed on Sep. 19, 2007.

(30) Foreign Application Priority Data

Sep. 18, 2007 (EP) .................... 07116679

(51) Int. Cl.
*C07C 211/00* (2006.01)
*A61K 8/00* (2006.01)
*A61K 8/18* (2006.01)

(52) U.S. Cl. ......................... 564/306; 424/59

(58) Field of Classification Search .......... None
See application file for complete search history.

(56) References Cited

U.S. PATENT DOCUMENTS

| | | | |
|---|---|---|---|
| 2,617,827 A | 11/1952 | McKeever et al. |
| 4,045,229 A | 8/1977 | Weber, II et al. |
| 4,195,999 A | 4/1980 | Adachi et al. |
| 4,504,644 A | 3/1985 | Lang et al. |
| 4,719,166 A | 1/1988 | Blevins et al. |
| 4,824,902 A | 4/1989 | Chen |
| 4,839,160 A | 6/1989 | Forestier et al. |
| 4,866,159 A | 9/1989 | Forestier et al. |
| 4,950,467 A | 8/1990 | Phalangas et al. |
| 5,338,532 A | 8/1994 | Tomalia et al. |
| 5,945,091 A | 8/1999 | Habeck et al. |
| 6,238,648 B1 | 5/2001 | Leusch et al. |
| 6,358,496 B1 | 3/2002 | Zink et al. |
| 6,916,778 B1 | 7/2005 | Detering et al. |
| 7,407,648 B2 | 8/2008 | Wagner et al. |
| 7,510,703 B2 | 3/2009 | Richard |
| 2005/0255055 A1 | 11/2005 | Wagner et al. |
| 2008/0260661 A1 | 10/2008 | Kluijtmans et al. |
| 2009/0130033 A1 | 5/2009 | Kluijtmans et al. |

FOREIGN PATENT DOCUMENTS

| | | |
|---|---|---|
| EP | 0 331 494 A2 | 9/1989 |
| EP | 0 412 570 B1 | 7/1996 |
| EP | 1 273 308 A1 | 1/2003 |
| EP | 0 895 776 B1 | 6/2003 |
| EP | 1 172 399 B1 | 4/2005 |
| EP | 1 728 501 A1 | 12/2006 |
| FR | 2757389 A1 | 12/1996 |
| WO | WO-00/20388 A1 | 4/2000 |
| WO | WO-00/65142 A1 | 11/2000 |
| WO | WO-01/08647 A1 | 2/2001 |
| WO | WO-2004/006878 A1 | 1/2004 |
| WO | WO-2004/075871 A1 | 9/2004 |
| WO | WO-2005/058269 A1 | 6/2005 |
| WO | WO-2006/003094 A2 | 1/2006 |
| WO | WO-2006/009451 A1 | 1/2006 |
| WO | WO-2006/016806 A1 | 2/2006 |
| WO | WO-2006/032741 A1 | 3/2006 |
| WO | WO 2006/125676 A1 | 11/2006 |
| WO | WO-2007/014848 A2 | 2/2007 |
| WO | WO-2007/071582 A1 | 6/2007 |

OTHER PUBLICATIONS

Pourzand et al., Proc. Natl. Acad. Sci. USA, vol. 96, Jun. 1999, pp. 6751-6756.
Sestili et al., Free Radical Biology & Medicine [US], vol. 25, No. 2, Jul. 15, 1998, pp. 196-200.
Database Beilstein [Online] 1-19 Beilstein Institute for Organic Chemistry, Frankfurt-Main, DE; XP002506878 Database accession No. reaction ID: 636120 & Zhumal Obsshcei Khimii, 28, 1958, 1066-1071 abstract.
International Search Report corresponding to PCT/NL2008/050614, dated Jan. 21, 2009, 3 pages.

*Primary Examiner* — Susanna Moore
*Assistant Examiner* — Jennifer C Sawyer
(74) *Attorney, Agent, or Firm* — Gilberto M. Villacorta; Sunit Talapatra; Foley & Lardner LLP

(57) ABSTRACT

The invention relates to new, highly efficient UV-absorbing compounds, a process for their manufacturing and to uses of these UV-absorbing compounds. The UV-absorbing compounds are in particular UV-A-absorbing compounds according to Formula (VI) or (VII):

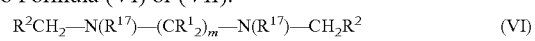
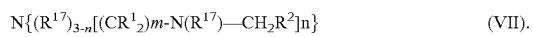

11 Claims, 1 Drawing Sheet

UV ABSORBING COMPOUNDS

CROSS-REFERENCE TO RELATED APPLICATIONS

This is a National Stage application of PCT/NL2008/050614, filed Sep. 18, 2008, which claims the benefit and priority of European Patent Application No. 07116679.7, filed Sep. 18, 2007 and U.S. Provisional Application No. 60/973,485, filed Sep. 19, 2007. The foregoing applications are incorporated by reference herein in their entirety.

FIELD OF THE INVENTION

The present invention is in the field of UV-absorbing compounds and their use in sunscreen compositions and other cosmetic applications.

BACKGROUND OF THE INVENTION

The detrimental effects of exposing the skin to UV-light are manifold and are well documented in the prior art. In particular, it is well known that UV-B radiation (wavelength of about 290 to about 315 nm) causes erythematic disorders or sunburn whereas UV-A radiation (wavelength from about 315 to about 400 nm) causes phototoxic and photochemical reactions.

The use of organic UV-absorbing compounds for sunscreen applications is also widely known. A disadvantage of organic UV-absorbing compounds is their low water solubility. Hydrophobic UV-absorbing compounds, with or without the combination with organic solvents, are capable of passing the so-called stratum corneum with the risk of entering the bloodstream.

A further disadvantage of many organic UV-absorbing compounds is that they are unstable under UV-light and prone to degradation. UV-exposure can cause photochemical reactions that destroy the UV-absorbing compound thereby reducing the protection against UV radiation in time.

U.S. Pat. No. 4,045,229 discloses photographic elements comprising a support, a radiation sensitive silver halide emulsion layer and a UV-absorbing 1-amino-4-cyano-1,3-butadiene compound.

U.S. Pat. No. 4,839,160 discloses a cosmetic formulation for protecting the skin against UV-radiation comprising a UV-absorbing polymer of benzylidenenobornanone units having $C_4$-$C_{12}$ alkoxy chains.

UV-A and UV-B absorbing compounds coupled through an oxygen or nitrogen atom to a polyacrylic backbone are known from WO 2001/08647. These products are substantially insoluble particles and are formulated with a carrier into sunscreen compositions, said carrier being capable of being absorbed by the substantially insoluble particles, altering the refractive index of the sunscreen composition and rendering the sunscreen composition essentially transparent to the skin. As a carrier, oily (i.e. strongly hydrophobic) components such as tocopherol or a functional analogue or derivative thereof, a vegetable oil, a mineral oil or a silicone oil, is used which enhances the risk of skin penetration.

WO 2000/065142 discloses polymers with broad UV-absorption for protection of textile materials against UV-radiation by adhering these polymers to textile fibres. However, WO 2000/065142 is silent with respect to sunscreen compositions.

FR A 2.757.389 discloses the combined use of UV-absorbing compounds and a hyperbranched or dendrimeric polymer in sunscreen formulations.

WO 2004/006878 discloses merocyanine derivatives for cosmetic use, in particular sunscreen formulations.

WO 2004/075871 discloses cosmetic compositions for protection against UV-A-radiation comprising for example a product obtained by coupling aminobutadienes and a polymer having free amino groups.

WO 2005/058269 discloses merocyanine compounds as UV-A absorbers. These compounds can be used both in dissolved form and in the micronized state.

WO 2006/003094 discloses merocyanine derivatives and oligomers thereof for protecting human hair and skin against the damaging effect of UV-A-radiation.

WO 2006/009451 discloses dendrimer-aminobutadiene-based UV-A-protecting products.

WO 2006/032741 discloses silane merocyanine sulphone derivatives, compositions comprising such silane merocyanine sulphone derivatives and the use of these compositions as UV protecting products.

WO 2006/125676 discloses a method for improving the photochemical stability of UV-A protecting dibenzoylmethane compounds by combining these with a merocyanine sulphone derivative and compositions comprising a UV-A-protecting dibenzoylmethane compound and a merocyanine sulphone derivative.

EP 1.728.501 A1 discloses a cosmetic preparation comprising at least an UV-A-light protection filter, which is bound to a polypeptide, at least an UV-B-light protection filter and/or a broadband filter.

WO 2006/016806 discloses the use of UV-A-absorbing compounds in cosmetic compositions.

WO 2007/014848 discloses the use of merocyanine derivatives and oligomers thereof for protecting body-care and household products from photolytic and oxidative degradation.

WO 2007/071582 discloses the use of merocyanine derivatives for protecting body-care and household products against the harmful effect of UV-radiation.

In spite of these attempts, there remains a need for UV-absorbing components which provide sufficient direct protection against sunlight by absorbing UV-radiation while not showing substantial penetration through the skin. There is also a need for UV-absorbing components that are substantially transparent for visible light radiation. In addition, there is a need for UV-absorbing components that are heat and UV-light stable and which are well soluble or dispersable in ingredients used in cosmetic compositions.

SUMMARY OF THE INVENTION

It is an object of this invention to provide new, highly efficient, UV-absorbing compounds.

It is a further object of the invention to provide a UV-absorbing compound that can easily be formulated into a sunscreen composition without giving emulsion stability problems.

A further object of the invention is to provide a sunscreen composition comprising a UV-absorbing compound which is substantially transparent in the visible light region (i.e. above about 400 nm to about 800 nm).

Another object of the invention is to provide a sunscreen composition comprising a UV-absorbing compound which can be applied in high concentrations and which is substantially stable against degradation induced by heat and/or UV-light.

Another object of the invention is to provide a sunscreen composition comprising a UV-absorbing compound which does substantially not penetrate the skin thereby minimizing risks of undesired, in particular immunogenic or allergic side effects.

A further object of the present invention is to provide a UV-absorbing compound having a high solubility or dispersability in cosmetic ingredients such as cosmetic oils.

Another object of the present invention is to provide a process for the preparation of a UV-absorbing compound having the advantageous properties listed above.

The present invention therefore relates to a process for the preparation of an UV-absorbing compound, wherein:
(a) a polyamine according to Formula (I):

$$NH_{3-n}[(CR^1{}_2)_m\text{—}NH_2]_n \quad (I)$$

wherein:
n=1-3,
m=2-12, and
each $R^1$ is independently selected from a hydrogen atom, a $C_1$-$C_6$ alkyl group or a $C_1$-$C_6$ alkoxy group,
is reacted with an aldehyde $R^2$—C(O)H, wherein $R^2$ is selected from the group consisting of a hydrogen atom, a $C_1$-$C_{20}$ alkyl group, a $C_2$-$C_{20}$ alkenyl group, a $C_2$-$C_{20}$ alkynyl group, a $C_6$-$C_{20}$ aryl group and a group of the formula —$(CR^{18}{}_2)_o NHCH_2 R^3$, wherein o=1-11, each $R^{18}$ is independently selected from a hydrogen atom, a $C_1$-$C_6$ alkyl group or a $C_1$-$C_6$ alkoxy group and $R^3$ is a hydrogen atom, a $C_1$-$C_{20}$ alkyl group, a $C_6$-$C_{20}$ aryl group or a group of the formula —$(CR^{18}{}_2)_p NHCH_2 R^4$, wherein p=1-11, $R^{18}$ is as defined above and $R^4$ is a hydrogen atom, a $C_1$-$C_{20}$ alkyl group, a $C_6$-$C_{20}$ aryl group or a group of the formula —$(CR^{18}{}_2)_q NHCH_2 R^5$, wherein q=1-11, $R^{18}$ is as defined above and $R^5$ is a hydrogen atom, a $C_1$-$C_{20}$ alkyl group or a $C_6$-$C_{20}$ aryl group; and preferably subsequently followed by a reduction step,
to form a polyamine according Formula (II) for n=2 or 3

$$NH_{3-n}[(CR^1{}_2)_m\text{—}NH\text{—}CH_2 R^2]_n \quad (II)$$

or a polyamine according to Formula (III) for n=1

$$R^2 CH_2\text{—}NH\text{—}(CR^1{}_2)_m\text{—}NH\text{—}CH_2 R^2 \quad (III)$$

(b) the polyamine according to Formula (II) or the polyamine according to Formula (III) is reacted with an aminobutadiene derivative according to Formula (IV):

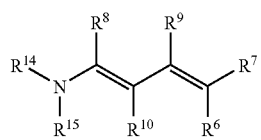

(IV)

wherein:
$R^6$ and $R^7$ are independently selected from the group consisting of —CN, —C(O)OH, —C(O)OR$^{11}$, —C(O)R$^{11}$ and —S(O$_2$)R$^{11}$, wherein R$^{11}$ is a $C_6$-$C_{20}$ aryl group or a $C_1$-$C_{25}$ alkyl group, wherein in one embodiment the $C_1$-$C_{25}$ alkyl group is optionally substituted with one or more hetero-atom containing groups, the hetero-atom being selected from O, N, S and Si, and wherein two R$^{11}$ groups optionally form a ring structure if the R$^{11}$ groups are $C_1$-$C_{25}$ alkyl groups, said ring structure being a five to seven membered ring structure and optionally comprising a hetero-atom, said hetero-atom being selected from the group consisting of N, O and S, and/or an oxo group;

$R^8$, $R^9$ and $R^{10}$ are independently selected from the group consisting of hydrogen, a $C_1$-$C_{20}$ alkyl group, a $C_3$-$C_{20}$ alkenyl group, a $C_3$-$C_{20}$ alkynyl group, a $C_7$-$C_{20}$ arylalkyl group, —CN, —OR$^{12}$, —SR$^{12}$ and —N(R$^{12}$R$^{13}$), wherein R$^{12}$ and R$^{13}$ are independently selected from the group consisting of hydrogen, a $C_1$-$C_{20}$ alkyl group and a $C_6$-$C_{20}$ aryl group; wherein R$^8$ and R$^9$, R$^8$ and R$^{10}$ or R$^9$ and R$^{10}$ optionally form a ring structure, said ring structure optionally comprising a hetero-atom, said hetero-atom being selected from the group consisting of N, O and S, and/or an oxo group;

$R^{14}$ is selected from an optionally substituted $C_6$-$C_{20}$ aryl group, preferably a $C_6$-$C_{12}$ aryl group, wherein the substituents are preferably selected from the group consisting of nitro, hydroxy, cyano, $C_1$-$C_4$ alkoxy, $C_1$-$C_{20}$ (preferably $C_1$-$C_{14}$) alkyl, halide, carboxy and amino;

$R^{15}$ is selected from —C(O)R$^{16}$ and —S(O$_2$)R$^{16}$, wherein R$^{16}$ is $C_1$-$C_{20}$ alkyl.

If desired in the process more than one aminobutadiene derivative according formula (IV) may be used (a mixture of compounds differing is substituents R$^6$, R$^7$, R$^8$, R$^9$ and/or R$^{10}$; if desired, for instance for synthesis reasons, also substituents R$^{14}$ and R$^{15}$ may constitute a mixture).

The present invention also relates to the UV absorbing compounds per se and to mixtures comprising these compounds.

The present invention further relates to the use of the UV absorbing compounds for cosmetic use, in particular sunscreen formulations.

DETAILED DESCRIPTION OF THE INVENTION

Definitions

Figure 1:
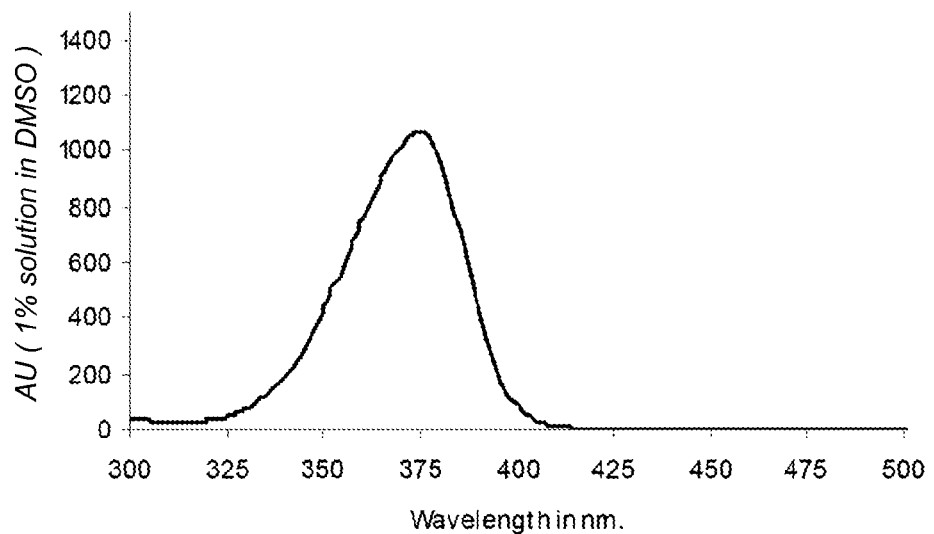
FIG. 1 shows a representative absorption spectrum of a compound according to the invention.

The verb "to comprise" as is used in this description and in the claims and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

In this document, the terms "alkylaryl group" and "arylalkyl group" denote hydrocarbyl groups wherein the number of carbon atoms refer to the carbon atoms of both the alkyl and the aryl group. Additionally, whereas an "alkylaryl group" denotes an aryl group substituted with one or more alkyl groups, an "arylalkyl group" denotes an alkyl group substituted with one or more aryl groups. Well known examples of an alkylaryl group are the tolyl group and the xylyl group and well known examples of an arylalkyl group are the benzyl group and the diphenylmethyl group. The alkylaryl group and arylalkyl groups are optionally further substituted, preferably with heteroatom containing groups, wherein the heteroatom is preferably selected from halide, O, N and S. Well known examples of such substituents include —CN, —OH, —OCH$_3$, —NH$_2$, —NMeH, —NO$_3$, —Cl, —Br, —I and —SH. Substituents may also be alkyl or aryl groups e.g. a $C_{16}$ arylalkyl group may for instance be a diphenylbutyl group, an alkyl substituted diphenylmethyl group, e.g. 1-(3-methy-1,4- methoxy-phenyl)-1-(3,4-dimethylphenyl)-methyl, or an alkyl group substituted by a phenyl group that may be substituted by alkyl groups, e.g. 2-(2,3,5-trimethylphenyl)-3-methyl-5-chloro-hexyl.

"Aryl groups" generally refer to monocyclic or polycyclic aromatic hydrocarbyl groups. Further, in this document, the terms "alkyl", "alkenyl", "alkynyl", alkoxy etc. denote saturated and unsaturated aliphatic hydrocarbyl groups which may be linear, branched or cyclic. Additionally, alkenyl groups and alkynyl groups may comprise more than one carbon-carbon double and/or triple bonds. Obviously, the alkyl, alkenyl, alkynyl, alkoxy groups etc. are optionally further substituted, preferably with heteroatom containing groups, wherein the heteroatom is preferably selected from halide, O, N, S and Si.

Also in this document a ring structure is to be understood as a four to eight membered ring structure, preferably a five to seven membered ring structure, which optionally comprises a heteroatom within the ring structure, wherein the hetero-atom is preferably selected from O, N and S. The ring structure may also be further substituted, preferably with a hetero-atom containing group, wherein the hetero-atom is preferably selected from O, N and S, or the ring structure may comprise an oxo group (═O).

Preferred Embodiments of the Process

In general terms, the process according to the present invention involves essentially a reaction between a compound having at least two secondary amine groups and an aminobutadiene derivative being reactive towards secondary amine groups. In this process, it is preferred that all secondary amine groups are converted whereas any tertiary amine group is unaffected. A preferred aminobutadiene derivative is the aminobutadiene derivative according to Formula (IV).

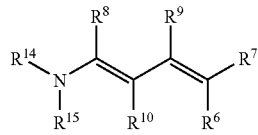

(IV)

wherein:
$R^6$ and $R^7$ are independently selected from the group consisting of —CN, —C(O)OH, —C(O)OR$^{11}$, —C(O)R$^{11}$ and —S(O$_2$)R$^{11}$, wherein R$^{11}$ is a C$_6$-C$_{20}$ aryl group or a C$_1$-C$_{25}$ alkyl group, wherein in one embodiment the C$_1$-C$_{25}$ alkyl group is optionally substituted with one or more hetero-atom containing groups, the hetero-atom being selected from O, N, S and Si, and wherein two R$^{11}$ groups optionally form a ring structure if the R$^{11}$ groups are C$_1$-C$_{25}$ alkyl groups, said ring structure being a five to seven membered ring structure and optionally comprising a hetero-atom, said hetero-atom being selected from the group consisting of N, O and S, and/or an oxo group;
$R^8$, $R^9$ and $R^{10}$ are independently selected from the group consisting of hydrogen, a C$_1$-C$_{20}$ alkyl group, a C$_3$-C$_{20}$ alkenyl group, a C$_3$-C$_{20}$ alkynyl group, a C$_7$-C$_{20}$ arylalkyl group, —CN, —OR$^{12}$, —SR$^{12}$ and —N(R$^{12}$R$^{13}$), wherein R$^{12}$ and R$^{13}$ are independently selected from the group consisting of hydrogen, a C$_1$-C$_{20}$ alkyl group and a C$_6$-C$_{20}$ aryl group; wherein R$^8$ and R$^9$, R$^8$ and R$^{10}$ or R$^9$ and R$^{10}$ optionally form a ring structure, said ring structure optionally comprising a hetero-atom, said heteroatom being selected from the group consisting of N, O and S, and/or an oxo group;
$R^{14}$ is selected from an optionally substituted C$_6$-C$_{20}$ aryl group, preferably a C$_6$-C$_{12}$ aryl group, wherein the substituents are preferably selected from the group consisting of nitro, hydroxy, cyano, C$_1$-C$_4$ alkoxy, C$_1$-C$_{20}$ (preferably C$_1$-C$_{14}$) alkyl, halide, carboxy and amino;
$R^{15}$ is selected from —C(O)R$^{16}$ and —S(O$_2$)R$^{16}$, wherein R$^{16}$ is C$_1$-C$_{20}$ alkyl.

Substituents R$^{14}$ and R$^{15}$ are preferably selected to form good leaving groups in the reaction with the polyamine according formula (II) or formula (III). Suitable substituents are e.g. for R$^{14}$ phenyl or substituted phenyl groups combined with for R$^{15}$-acetyl groups.

If R$^8$, R$^9$ or R$^{10}$ is a —N(R$^{12}$R$^{13}$) group it is preferred that R$^{12}$ and R$^{13}$ are not both hydrogen.

The present invention therefore relates to a process for the preparation of an UV-absorbing compound, wherein a polyamine according to Formula (I):

$$NH_{3-n}[(CR^1_2)_m—NH_2]_n \qquad (I)$$

wherein:
n=1-3,
m=2-12, and
each R$^1$ is independently selected from a hydrogen atom, a C$_1$-C$_6$ alkyl group or a C$_1$-C$_6$ alkoxy group, is reacted with an aldehyde R$^2$—C(O)H,
wherein R$^2$ is selected from the group consisting of a hydrogen atom, a C$_1$-C$_{20}$ alkyl group, a C$_2$-C$_{20}$ alkenyl group, a C$_2$-C$_{20}$ alkynyl group, a C$_6$-C$_{20}$ aryl group and a group of the formula —(CR$^{18}_2$)$_o$NHCH$_2$R$^3$, wherein o=1-11, each R$^{18}$ is independently selected from a hydrogen atom, a C$_1$-C$_6$ alkyl group or a C$_1$-C$_6$ alkoxy group and R$^3$ is a hydrogen atom, a C$_1$-C$_{20}$ alkyl group, a C$_6$-C$_{20}$ aryl group or a group of the formula —(CR$^{18}_2$)$_p$ NHCH$_2$R$^4$, wherein p=1-11, R$^{18}$ is as defined above and R$^4$ is a hydrogen atom, a C$_1$-C$_{20}$ alkyl group, a C$_6$-C$_{20}$ aryl group or a group of the formula —(CR$^{18}_2$)$_q$ NHCH$_2$R$^5$, wherein q=1-11, R$^{18}$ is as defined above and R$^5$ is a hydrogen atom, a C$_1$-C$_{20}$ alkyl group or a C$_6$-C$_{20}$ aryl group; and preferably subsequently followed by a reduction step to form a polyamine according Formula (II) for n=2 or 3

$$NH_{3-n}[(CR^1_2)_m—NH—CH_2R^2]_n \qquad (II)$$

or a polyamine according to Formula (III) for n=1

$$R^2CH_2—NH—(CR^1_2)_m—NH—CH_2R^2 \qquad (III)$$

and subsequently the polyamine according to Formula (II) or the polyamine according to Formula (III) is reacted with an aminobutadiene derivative according to Formula (IV) as described above.

Most preferred is an aminobutadiene derivative according to Formula (V), wherein R$^6$, R$^7$, R$^8$, R$^9$ and R$^{10}$ are as defined above:

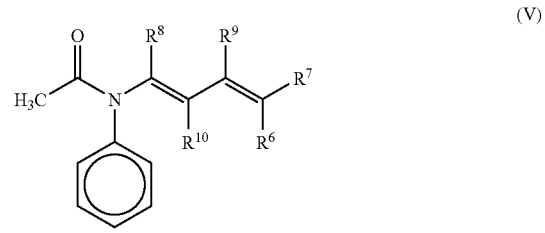

(V)

Aminobutadiene derivatives may be synthesized as described in the prior art, for instance as described in U.S. Pat. No. 4,551,420, U.S. Pat. No. 4,719,166, U.S. Pat. No. 4,195,999, U.S. Pat. No. 4,045,229, WO 2007/071582, WO 2002/034710, US 2003/0181483 and JP 2003277348, the contents of which are incorporated herein by reference. Polyamines according formula (I) may be prepared as described in e.g. U.S. Pat. No. 4,895,840, WO 2005/092282 and by R. Moors et al, Chem. Ber., 126, 2133-2135, 1993, which are all incorporated herein by reference. Many polyamines are commercially available.

In the event that the compound having at least two secondary amine groups also comprises one or more primary amine groups, the latter can also first be converted with a compound having a reactive group that is complementary reactive with a primary amine group. However, it is preferred that when the compound having at least two secondary amine groups also comprises one or more primary amine groups, it is converted with the compound having a reactive group that is complementary reactive with a primary amine group. It is then preferred that this compound that is complementary reactive with the primary amine group is sufficiently bulky or is sufficiently substituted to provide the necessary bulkiness to make the conversion of the primary amine groups sufficiently selective.

Consequently, in its broadest aspect, the present invention relates to a process for the preparation of an UV-absorbing compound wherein a polyamine having at least two primary or secondary amine groups, wherein the total of amine groups is in the range of 2-12, is optionally reacted in a first step with a compound having a reactive group that is complementary reactive with a primary amine group, said compound having a reactive group that is complementary reactive with a primary amine group being a compound according to the formula $R^2$—C(O)H, wherein $R^2$ is selected from the group consisting of a hydrogen atom, a $C_1$-$C_{20}$ alkyl group, a $C_2$-$C_{20}$ alkenyl group, a $C_2$-$C_{20}$ alkynyl group, a $C_6$-$C_{20}$ aryl group and a group of the formula —$(CR^{18}_2)_o$NHCH$_2R^3$, wherein o=1-11, each $R^{18}$ is independently selected from a hydrogen atom, a $C_1$-$C_6$ alkyl group or a $C_1$-$C_6$ alkoxy group, and $R^3$ is a hydrogen atom, a $C_1$-$C_{20}$ alkyl group, a $C_6$-$C_{20}$ aryl group or a group of the formula —$(CR^{18}_2)_p$NHCH$_2R^4$, wherein p=1-11, each $R^{18}$ is as defined above and $R^4$ is a hydrogen atom, a $C_1$-$C_{20}$ alkyl group, a $C_6$-$C_{20}$ aryl group or a group of the formula —$(CR^{18}_2)_q$NHCH$_2R^5$, wherein q=1-11, each $R^{18}$ is as defined above and $R^5$ is a hydrogen atom, a $C_1$-$C_{20}$ alkyl group or a $C_6$-$C_{20}$ aryl group, to form a substituted polyamine having at least two secondary amine groups; and the substituted polyamine having at least two secondary amine groups is reacted with an aminobutadiene derivative being reactive towards secondary amine groups. As disclosed above, it is preferred that the aminobutadiene derivative is the compound according to Formula (IV), most preferred the compound according to Formula (V). Additionally, it is preferred that all secondary amine groups are converted without conversion of any tertiary amine group.

It is preferred that in the first step all primary amine groups are converted into secondary amine groups and that in the second step all secondary amine groups react with the aminobutadiene derivative. The resulting compound preferably only comprises tertiary amine groups and no primary or secondary amine groups. It was found that compounds having primary or secondary amine groups exhibit a much lower stability against degradation by heat. So the main inventive concept is a polyamine in which the N atoms of all aminobutadiene groups are tertiary. This important aspect for improved stability is not disclosed or suggested in the prior art.

Preferably the compound of the invention comprises at least three aminobutadiene groups by which a higher extinction value can be achieved. Preferably the molecular weight of the compound of the invention is not too low since small molecules tend to penetrate into the skin which is not desired.

In order to make the conversion reaction from primary to secondary amine groups sufficiently selective the reactive group, preferably the aldehyde $R^2$—C(O)H, is preferably bulky. Accordingly, to prevent overalkylation, in a preferred embodiment $R^2$ is selected from the group consisting of a $C_5$-$C_{20}$ alkyl group (preferably a $C_6$-$C_{20}$ alkyl group), a $C_5$-$C_{20}$ alkenyl group (preferably a $C_6$-$C_{20}$ alkenyl group), a $C_5$-$C_{20}$ alkynyl group (preferably a $C_6$-$C_{20}$ alkynyl group), a $C_6$-$C_{20}$ aryl group and a group of the formula —$(CR^{18}_2)_o$NHCH$_2R^3$, wherein o=1-11, each $R^{18}$ is independently selected from a hydrogen atom, a $C_1$-$C_6$ alkyl group or a $C_1$-$C_6$ alkoxy group and $R^3$ is a hydrogen atom, a $C_1$-$C_{20}$ alkyl group, a $C_6$-$C_{20}$ aryl group or a group of the formula —$(CR^{18}_2)_p$NHCH$_2R^4$, wherein p=1-11, each $R^{18}$ is as defined above and $R^4$ is a hydrogen atom, a $C_1$-$C_{20}$ alkyl group, a $C_6$-$C_{20}$ aryl group or a group of the formula —$(CR^{18}_2)_q$NHCH$_2R^5$, wherein q=1-11, each $R^{18}$ is as defined above and $R^5$ is a hydrogen atom, a $C_1$-$C_{20}$ alkyl group or a $C_6$-$C_{20}$ aryl group. The integers for o, p and q are more preferably 3-9, most preferably 4-7.

$R^{18}$ is more preferably hydrogen. Even more preferably $R^2$ is selected from the group consisting of a $C_6$-$C_{20}$ alkyl group, a $C_6$-$C_{20}$ alkenyl group, a $C_6$-$C_{20}$ alkynyl group and a $C_6$-$C_{20}$ aryl group.

Preferably the molecular weight of the compound of the invention is larger than about 600 Da, preferably larger than about 800 Da, since compounds having a lower molecular weight tend to penetrate into the skin which is not desired. Preferably the compound of the invention comprises at least three aminobutadiene groups.

According to a first preferred embodiment of the process according to the present invention, m is in the range of 5-12. According to this first preferred embodiment $R^1$, $R^2$, $R^3$, $R^4$, $R^5$, o, p and q are as defined above. Additionally, it is preferred that in this first preferred embodiment m=5-10, more preferably 5-8, even more preferably 6-8, and most preferably m=6.

According to a second preferred embodiment of the process according to the present invention, m is in the range of 2-4. According to this second preferred embodiment, $R^1$, $R^3$, $R^4$, $R^5$, o, p and q are as defined above, $R^2$ is selected from the group consisting of a $C_5$-$C_{20}$ alkyl group, more preferably a $C_6$-$C_{20}$ alkyl group, a $C_5$-$C_{20}$ alkenyl group, more preferably a $C_6$-$C_{20}$ alkenyl group, a $C_5$-$C_{20}$ alkynyl group, more preferably a $C_6$-$C_{20}$ alkynyl group, a $C_6$-$C_{20}$ aryl group and a group of the formula —$(CR^{18}_2)_o$NHCH$_2R^3$, wherein o=1-11, each $R^{18}$ is independently selected from a hydrogen atom, a $C_1$-$C_6$ alkyl group or a $C_1$-$C_6$ alkoxy group, and $R^3$ is a hydrogen atom, a $C_1$-$C_{20}$ alkyl group, a $C_6$-$C_{20}$ aryl group or a group of the formula —$(CR^{18}_2)_p$NHCH$_2R^4$, wherein p=1-11, each $R^{18}$ is as defined above and $R^4$ is a hydrogen atom, a $C_1$-$C_{20}$ alkyl group, a $C_6$-$C_{20}$ aryl group or a group of the formula —$(CR^{18}_2)_q$NHCH$_2R^5$, wherein q=1-11, each $R^{18}$ is as defined above and $R^5$ is a hydrogen atom, a $C_1$-$C_{20}$ alkyl group or a $C_6$-$C_{20}$ aryl group. More preferably o, p and q are 3-9, even more preferably 4-7 for the reasons as specified above. $R^{18}$ is more preferably hydrogen.

Another general inventive concept of the UV-absorbing compounds according to both first and second preferred embodiment of the process according to the present invention is that these UV-absorbing compounds must have a sufficient solubility, because excellent compatibility with commonly used ingredients is desired. For example, an aspect of consideration is the solubility of the UV-absorbing compounds according to the present invention in solvents like Finsolv™ TN, a commonly used $C_{12}$-$C_{15}$ alkyl benzoate oil. For smaller integers for m, i.e. m=2-4, the solubility is less than for larger integers for m, i.e. m=5-12. However, if smaller integers for m, i.e. m=2-4, are selected, it is preferred that the various substituents of the nitrogen atoms are more hydrophobic groups. Preferably $R^2$, $R^6$ and/or $R^7$ are more hydrophobic groups. Thus $R^6$ and $R^7$ are preferably selected from the group consisting of —C(O)O$R^{11}$, —C(O)$R^{11}$ and —S(O$_2$)$R^{11}$, wherein $R^{11}$ is a $C_6$-$C_{20}$ aryl group or a $C_6$-$C_{25}$ alkyl group; $R^2$ is preferably selected from the group consisting of a $C_6$-$C_{20}$ alkyl group, a $C_6$-$C_{20}$ alkenyl group, a $C_6$-$C_{20}$ alkynyl group, a $C_6$-$C_{20}$ aryl group and a group of the formula —(C$R^{18}$$_2$)$_o$NHCH$_2$$R^3$, wherein o=1-11, preferably o=3-9, each $R^{18}$ is independently selected from a hydrogen atom, a $C_1$-$C_6$ alkyl group or a $C_1$-$C_6$ alkoxy group and $R^3$ is a hydrogen atom, a $C_1$-$C_{20}$ alkyl group, a $C_6$-$C_{20}$ aryl group or a group of the formula —(C$R^{18}$$_2$)$_p$NHCH$_2$$R^4$, wherein p=1-11, preferably p=3-9, each $R^{18}$ is as defined above and $R^4$ is a hydrogen atom, a $C_1$-$C_{20}$ alkyl group, a $C_6$-$C_{20}$ aryl group or a group of the formula —(C$R^{18}$$_2$)$_q$NHCH$_2$$R^5$, wherein q=1-11, preferably q=3-9, each $R^{18}$ is as defined above and $R^5$ is a hydrogen atom, a $C_1$-$C_{20}$ alkyl group or a $C_6$-$C_{20}$ aryl group. Even more preferably $R^2$ is selected from the group consisting of a $C_6$-$C_{20}$ alkyl group, a $C_6$-$C_{20}$ alkenyl group, a $C_6$-$C_{20}$ alkynyl group and a $C_6$-$C_{20}$ aryl group. The first preferred embodiment is, however, preferred over the second preferred embodiment, because it was found that higher yields can be obtained for larger integers for m, presumably as a result of less steric hindrance in the reaction of the polyamine with the aminobutadiene derivative.

Substituents are preferably selected to yield compounds that are obtainable as a powder in crystalline and/or in amorphous form. A paste is less preferred because a paste is more difficult to handle. Therefore the melting point of the compounds of the invention is preferably higher than 20° C., more preferably higher than 30° C. The average size of the crystals or particles is preferably between 20 and 1000 μm, more preferably between 50 and 300 μm. Very small crystals/particles are generally sticky or may easily contaminate the air; large particles/crystals tend too dissolve more difficult and are also less preferred.

An additional advantage of the compounds of the current invention is their transparency, preferably their transparency for visible light; the compounds have almost no colour which is an advantage for most formulations that require application to the human skin.

For step (a) of both first and second preferred embodiments of the process according to the present invention, it is preferred that the polyamine according to Formula (I) is reacted with the aldehyde $R^2$—C(O)H in a molar ratio of ranging from 1:1 to 1:1.1 with respect to the amount of primary amine groups present in Formula (I).

For step (b) of both first and second preferred embodiments of the process according to the present invention, it is preferred that the polyamine according to Formula (II) or Formula (III) is reacted with the aminobutadiene derivative according to Formula (IV) in a molar ratio of ranging from 1:1 to 1:1.1 with respect to the number of secondary amine groups present in Formula (II) or Formula (III).

For both first and second preferred embodiments, it is preferred that n is 2 or 3, it is even more preferred that n is 2. It is furthermore preferred that $R^2$ is a $C_6$-$C_{20}$ alkyl group, a $C_6$-$C_{20}$ alkenyl group, a $C_6$-$C_{20}$ alkynyl group or a $C_6$-$C_{20}$ aryl group, most preferred a $C_6$-$C_{20}$ alkyl group or a $C_6$-$C_{20}$ aryl group. Preferably, $R^1$, $R^8$, $R^9$ and $R^{10}$ are hydrogen. $R^{18}$ is preferably hydrogen. It is also preferred that $R^6$ is S(O$_2$)$R^{11}$, wherein $R^{11}$ is a $C_6$-$C_{20}$ aryl group, more preferably a $C_6$ aryl group. It is furthermore preferred that $R^7$ is C(O)O$R^{11}$, wherein $R^{11}$ is a $C_1$-$C_{25}$ alkyl group, more preferably a $C_1$-$C_{12}$, most preferably a $C_4$-$C_{12}$ alkyl group. $R^{14}$ is preferably a $C_6$ aryl group and $R^{15}$ is preferably —C(O)CH$_3$ (methylcarbonyl).

If desired in the process more than one aminobutadiene derivative according formula (IV) may be used (a mixture of compounds differing is substituents $R^6$, $R^7$, $R^8$, $R^9$ and/or $R^{10}$; if desired, for instance for synthesis reasons, also substituents $R^{14}$ and $R^{15}$ may constitute a mixture).

The first step of the synthesis is most preferably the conversion of the primary amines of the starting structure to a secondary amine by means of reaction with an aldehyde followed by a reduction step. The reaction with the aldehyde can be performed in any suitable organic solvent. Especially low boiling alcohols such as ethanol and isopropanol are suitable. The reaction is preferably performed at room temperature but in case required other temperatures may be used. For example in case of less reactive aldehydes elevated reaction temperatures may be used, e.g. 40° C. or 60° C. The reaction time can vary from minutes to several days depending on the reactivity of the components. Following the reaction with the aldehyde a catalytic amount, e.g. from 1 mol % to 25 mol % with respect to the amount of primary amine groups, of a suitable reduction catalyst such as palladium/carbon catalyst is added to the reaction mixture and subsequent reaction is performed in hydrogen atmosphere in order to convert the formed imine to an amine. The amount of catalyst is preferably optimized for each combination of reactants but usually 10 mol % with respect to the amount of primary amine groups proved to be sufficient. The hydrogen pressure can vary between 1 and 50 atmosphere. Reaction times are typically in the order of hours and depend strongly on the hydrogen pressure. The higher the hydrogen pressure the shorter the reaction time. Yield of the above reactions are typically high >95%, yielding a relatively pure amine (>95%). The amine can be further purified in case required by techniques such as chromatography, salt formation and liberation, distillation, etc.

The coupling of the aminobutadiene to the amine thus obtained can most preferably be performed in many suitable solvents such as dimethylsulfoxide, tetrahydrofurane, dioxane, alcohols, esters, ethers, ketones. Preferably the reaction is performed in low boiling alcohols such as ethanol and iso-propanol. The reaction might be performed at any suitable temperature which does not deteriorate the compounds and gives the highest yield. Most preferable are temperatures ranging from −50 degrees Celcius up to reflux temperature. To reduce the formation of (colored) by-products the reaction pH is an important parameter. A pH between 6 and 8 is preferred. The pH of the reaction can be controlled by the addition of a buffer. The buffer might be organic or inorganic. Especially the combination of a phosphate buffer and an acetate buffer has proven to be effective. Reaction times typically vary from 1 hour to several days. Suitable isolation techniques of the final product depend on yield (purity) and character of the final product (solid/paste). Usual techniques such as filtration, evaporation, chromatography, crystallization, washing can be applied.

The UV-Absorbing Compounds

The UV-absorbing compounds according to the present invention are generally represented by Formula (VI) or (VII):

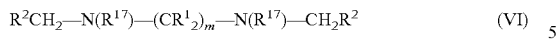   (VI)

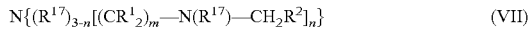   (VII)

wherein for Formula (VI)

m=2-12;

each $R^1$ is independently selected from a hydrogen atom, a $C_1$-$C_6$ alkyl group or a $C_1$-$C_6$ alkoxy group;

$R^2$ is selected from the group consisting of a hydrogen atom, a $C_1$-$C_{20}$ alkyl group, a $C_2$-$C_{20}$ alkenyl group, a $C_2$-$C_{20}$ alkynyl group, a $C_6$-$C_{20}$ aryl group and a group of the formula —$(CR^{18}_2)_oN(R^{17})CH_2R^3$, wherein o=1-11, each $R^{18}$ is independently selected from a hydrogen atom, a $C_1$-$C_6$ alkyl group or a $C_1$-$C_6$ alkoxy group and $R^3$ is a hydrogen atom, a $C_1$-$C_{20}$ alkyl group, a $C_6$-$C_{20}$ aryl group or a group of the formula —$(CR^{18}_2)_pN(R^{17})CH_2R^4$, wherein p=1-11, each $R^{18}$ is as defined above and $R^4$ is a hydrogen atom, a $C_1$-$C_{20}$ alkyl group, a $C_6$-$C_{20}$ aryl group or a group of the formula —$(CR^{18}_2)_qN(R^{17})CH_2R^5$, wherein q=1-11, each $R^{18}$ is as defined above and $R^5$ is a hydrogen atom, a $C_1$-$C_{20}$ alkyl group or a $C_6$-$C_{20}$ aryl group;

and wherein $R^{17}$ is selected from the group of substituents according to Formula (VIII):

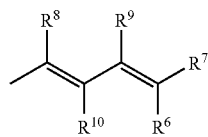   (VIII)

wherein $R^6$ and $R^7$ are independently selected from the group consisting of —C(O)OH, —$C(O)OR^{11}$, —$C(O)R^{11}$ and —$S(O_2)R^{11}$, wherein $R^{11}$ is a $C_6$-$C_{20}$ aryl group or a $C_1$-$C_{25}$ alkyl group, wherein in one embodiment the $C_1$-$C_{25}$ alkyl group is optionally substituted with one or more hetero-atom containing groups, the hetero-atom being selected from O, N, S and Si, and wherein two $R^{11}$ groups optionally form a ring structure if the $R^{11}$ groups are $C_1$-$C_{25}$ alkyl groups, said ring structure being a five to seven membered ring structure and optionally comprising a hetero-atom, said hetero-atom being selected from the group consisting of N, O, S, and an oxo group;

$R^8$, $R^9$ and $R^{10}$ are independently selected from the group consisting of hydrogen, a $C_1$-$C_{20}$ alkyl group, a $C_3$-$C_{20}$ alkenyl group, a $C_3$-$C_{20}$ alkynyl group, a $C_7$-$C_{20}$ arylalkyl group, —CN, —$OR^{12}$, —$SR^{12}$ and —$N(R^{12}R^{13})$, wherein $R^{12}$ and $R^{13}$ are independently selected from the group consisting of hydrogen, a $C_1$-$C_{20}$ alkyl group and a $C_6$-$C_{20}$ aryl group; wherein $R^8$ and $R^9$, $R^8$ and $R^{10}$ or $R^9$ and $R^{10}$ optionally form a ring structure, said ring structure optionally comprising a hetero-atom, said hetero-atom being selected from the group consisting of N, O, S, and an oxo group.

If $R^8$, $R^9$ or $R^{10}$ is a —$N(R^{12}R^{13})$ group it is preferred that $R^{12}$ and $R^{13}$ are not both hydrogen.

and wherein for Formula (VII)

n=2 or 3;

m=2-12;

each $R^1$ is independently selected from a hydrogen atom, a $C_1$-$C_6$ alkyl group or a $C_1$-$C_6$ alkoxy group;

$R^2$ is selected from the group consisting of a hydrogen atom, a $C_1$-$C_{20}$ alkyl group, a $C_2$-$C_{20}$ alkenyl group, a $C_2$-$C_{20}$ alkynyl group, a $C_6$-$C_{20}$ aryl group and a group of the formula —$(CR^{18}_2)_oN(R^{17})CH_2R^3$, wherein o=1-11, each $R^{18}$ is independently selected from a hydrogen atom, a $C_1$-$C_6$ alkyl group or a $C_1$-$C_6$ alkoxy group and $R^3$ is a hydrogen atom, a $C_1$-$C_{20}$ alkyl group, a $C_6$-$C_{20}$ aryl group or a group of the formula —$(CR^{18}_2)_pN(R^{17})CH_2R^4$, wherein p=1-11, each $R^{18}$ is as defined above and $R^4$ is a hydrogen atom, a $C_1$-$C_{20}$ alkyl group, a $C_6$-$C_{20}$ aryl group or a group of the formula —$(CR^{18}_2)_q N(R^{17})CH_2R^5$, wherein q=1-11, each $R^{18}$ is as defined above and $R^5$ is a hydrogen atom, a $C_1$-$C_{20}$ alkyl group or a $C_6$-$C_{20}$ aryl group;

and wherein $R^{17}$ is selected from the group of substituents according to Formula (VIII):

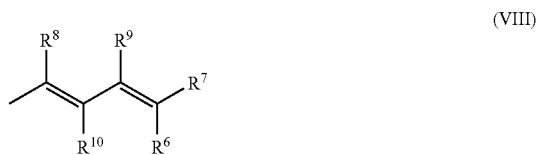   (VIII)

wherein $R^6$ and $R^7$ are independently selected from the group consisting of —CN, —C(O)OH, —$C(O)OR^{11}$, —$C(O)R^{11}$ and —$S(O_2)R^{11}$, wherein $R^{11}$ is a $C_6$-$C_{20}$ aryl group or a $C_1$-$C_{25}$ alkyl group, wherein in one embodiment the $C_1$-$C_{25}$ alkyl group is optionally substituted with one or more hetero-atom containing groups, the hetero-atom being selected from O, N, S and Si, and wherein two $R^{11}$ groups optionally form a ring structure if the $R^{11}$ groups are $C_1$-$C_{25}$ alkyl groups, said ring structure being a five to seven membered ring structure and optionally comprising a hetero-atom, said hetero-atom being selected from the group consisting of N, O, S, and an oxo group;

$R^8$, $R^9$ and $R^{10}$ are independently selected from the group consisting of hydrogen, a $C_1$-$C_{20}$ alkyl group, a $C_3$-$C_{20}$ alkenyl group, a $C_3$-$C_{20}$ alkynyl group, a $C_7$-$C_{20}$ arylalkyl group, —CN, —$OR^{12}$, —$SR^{12}$ and —$N(R^{12}R^{13})$, wherein $R^{12}$ and $R^{13}$ are independently selected from the group consisting of hydrogen, a $C_1$-$C_{20}$ alkyl group and a $C_6$-$C_{20}$ aryl group; wherein $R^8$ and $R^9$, $R^8$ and $R^{10}$ or $R^9$ and $R^{10}$ optionally form a ring structure, said ring structure optionally comprising a hetero-atom, said hetero-atom being selected from the group consisting of N, O, S, and an oxo group.

If $R^8$, $R^9$ or $R^{10}$ is a —$N(R^{12}R^{13})$ group it is preferred that $R^{12}$ and $R^{13}$ are not both hydrogen.

If in the process of making the compound (VI) or (VII) a mixture of compounds according formula (VIII) is used (differing is substituents $R^6$, $R^7$, $R^8$, $R^9$ and/or $R^{10}$) a mixture of compounds is formed. Usually however this is not preferred. Preferably the compound of the invention comprises at least three aminobutadiene groups.

According to a first preferred embodiment of the present invention, m=5-12. According to a second preferred embodiment of the present invention, m=2-4. The first preferred embodiment is preferred over the second preferred embodiment as is disclosed above.

If m=2-4, it is preferred that the second preferred embodiment excludes UV-absorbing compounds wherein $R^2$ is a hydrogen or a $C_1$-$C_5$ alkyl group. So for m=2-4 $R^2$ is preferably selected from the group consisting of a $C_6$-$C_{20}$ alkyl group, a $C_6$-$C_{20}$ alkenyl group, a $C_6$-$C_{20}$ alkynyl group, a $C_6$-$C_{20}$ aryl group and a group of the formula —$(CR^{18}_2)_o$N$(R^{17})CH_2R^3$, wherein o=1-11, preferably 3-9, each $R^{18}$ is independently selected from a hydrogen atom, a $C_1$-$C_6$ alkyl group or a $C_1$-$C_6$ alkoxy group and $R^3$ is a $C_1$-$C_{20}$ alkyl group, preferably a $C_6$-$C_{20}$ alkyl group, a $C_6$-$C_{20}$ aryl group or a group of the formula —$(CR^{18}_2)_p$N$(R^{17})CH_2R^4$, wherein p=1-11, preferably 3-9, each $R^{18}$ is as defined above and $R^4$ is a $C_1$-$C_{20}$ alkyl group, preferably a $C_6$-$C_{20}$ alkyl group, a $C_6$-$C_{20}$ aryl group or a group of the formula —$(CR^{18}_2)_q$N$(R^{17})CH_2R^5$, wherein q=1-11, preferably 3-9, each $R^{18}$ is as defined above and $R^5$ is a $C_1$-$C_{20}$ alkyl group, preferably a $C_6$-$C_{20}$ alkyl group, or a $C_6$-$C_{20}$ aryl group;

Also if m=5-12 more bulky $R^2$-groups are preferred to enhance the yield of the reaction. Thus $R^2$ is preferably selected from the group consisting of a $C_6$-$C_{20}$ alkyl group, a $C_6$-$C_{20}$ alkenyl group, a $C_6$-$C_{20}$ alkynyl group, a $C_6$-$C_{20}$ aryl group and a group of the formula —$(CR^{18}_2)_o$NHCH$_2R^3$, wherein o=1-11, each $R^{18}$ is independently selected from a hydrogen atom, a $C_1$-$C_6$ alkyl group or a $C_1$-$C_6$ alkoxy group and $R^3$ is a hydrogen atom, a $C_1$-$C_{20}$ alkyl group, a $C_6$-$C_{20}$ aryl group or a group of the formula —$(CR^{18}_2)_p$NHCH$_2R^4$, wherein p=1-11, each $R^{18}$ is as defined above and $R^4$ is a hydrogen atom, a $C_1$-$C_{20}$ alkyl group, a $C_6$-$C_{20}$ aryl group or a group of the formula —$(CR^{18}_2)_q$NHCH$_2R^5$, wherein q=1-11, each $R^{18}$ is as defined above and $R^5$ is a hydrogen atom, a $C_1$-$C_{20}$ alkyl group or a $C_6$-$C_{20}$ aryl group. The integers for o, p and q are more preferably 3-9, most preferably 4-7. Small integers for o, p and q lead to lower yields presumably due to steric effects, very high values make the structure very flexible which may make it more difficult to obtain the product in crystalline form. $R^{18}$ is more preferably hydrogen. Even more preferably $R^2$ is selected from the group consisting of a $C_6$-$C_{20}$ alkyl group, a $C_6$-$C_{20}$ alkenyl group, a $C_6$-$C_{20}$ alkynyl group and a $C_6$-$C_{20}$ aryl group, most preferably $C_6$-$C_{20}$ alkyl group or a $C_6$-$C_{20}$ aryl group.

In the group of UV-absorbing compounds according to Formula (VII), it is preferred that n is 2. According to the present invention, for compounds according Formulas (VI) and (VII) it is preferred that m is 5-12, preferably 5-10, more preferably 5-8, even more preferably 6-8 and most preferably m=6. It is also preferred that $R^1$, $R^8$, $R^9$ and $R^{10}$ are hydrogen. $R^{18}$ is preferably hydrogen. It is also preferred that $R^6$ is S(O$_2$)$R^{11}$, wherein $R^{11}$ is a $C_6$-$C_{20}$ aryl group, most preferably a $C_6$ aryl group. It is furthermore preferred that $R^7$ is C(O)OR$^{11}$, wherein $R^{11}$ is a $C_1$-$C_{25}$ alkyl group, more preferably a $C_1$-$C_{12}$ alkyl group or a $C_8$-$C_{25}$ alkyl group, most preferably a $C_8$ alkyl group. Finally, it is preferred that $R^2$ is a $C_6$-$C_{20}$ alkyl group, a $C_6$-$C_{20}$ alkenyl group, a $C_6$-$C_{20}$ alkynyl group or a $C_6$-$C_{20}$ aryl-group, more preferably a $C_6$-$C_{20}$ alkyl group or a $C_6$-$C_{20}$ aryl group, even more preferably a $C_6$-$C_{12}$ aryl-group, most preferably a $C_6$ aryl group.

Alternatively, certain compounds of the invention may be prepared by coupling the aminobutadiene derivative to a polyamine according formula (IX):

    (IX)

wherein m is 2-12, r is 1-6, each $R^1$ is independently selected from a hydrogen atom, a $C_1$-$C_6$ alkyl group or a $C_1$-$C_6$ alkoxy group, and $R^2$ is selected from the group consisting of a hydrogen atom, a $C_1$-$C_{20}$ alkyl group, a $C_2$-$C_{20}$ alkenyl group, a $C_2$-$C_{20}$ alkynyl group, a $C_6$-$C_{20}$ aryl group and a group of the formula —$(CR^{18}_2)_o$NHCH$_2R^3$, wherein o=1-11, each $R^{18}$ is independently selected from a hydrogen atom, a $C_1$-$C_6$ alkyl group or a $C_1$-$C_6$ alkoxy group and $R^3$ is a hydrogen atom, a $C_1$-$C_{20}$ alkyl group, a $C_6$-$C_{20}$ aryl group or a group of the formula —$(CR^{18}_2)_p$NHCH$_2R^4$, wherein p=1-11, $R^{18}$ is as defined above and $R^4$ is a hydrogen atom, a $C_1$-$C_{20}$ alkyl group, a $C_6$-$C_{20}$ aryl group or a group of the formula —$(CR^{18}_2)_q$NHCH$_2R^5$, wherein q=1-11, $R^{18}$ is as defined above and $R^5$ is a hydrogen atom, a $C_1$-$C_{20}$ alkyl group or a $C_6$-$C_{20}$ aryl group.

Compound (IX) can be prepared from the polyamine according formula (X) by reaction with an aldehyde $R^2$C(O)H according the method described above.

    (X)

A commercially available example of formula (X) is the polyamine tetraethylene pentamine (H$_2$N(CH$_2$)$_2$NH(CH$_2$)$_2$NH(CH$_2$)$_2$NH(CH$_2$)$_2$NH$_2$, available from Acros Organics).

The resulting product can be represented by formula (XI):

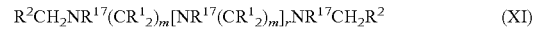    (XI)

wherein m, r, $R^1$ and $R^2$ are as defined above and $R^{17}$ is selected from the group of substituents according to Formula (VIII):

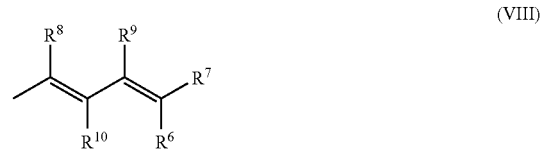    (VIII)

wherein
$R^6$ and $R^7$ are independently selected from the group consisting of —CN, —C(O)OH, —C(O)OR$^{11}$, —C(O)R$^{11}$ and —S(O$_2$)R$^{11}$, wherein $R^{11}$ is a $C_6$-$C_{20}$ aryl group or a $C_1$-$C_{25}$ alkyl group, wherein in one embodiment the $C_1$-$C_{25}$ alkyl group is optionally substituted with one or more hetero-atom containing groups, the hetero-atom being selected from O, N, S and Si; wherein two $R^{11}$ groups optionally form a ring structure if the $R^{11}$ groups are $C_1$-$C_{25}$ alkyl groups, said ring structure being a five to seven membered ring structure and optionally comprising a hetero-atom, said hetero-atom being selected from the group consisting of N, O, S, and an oxo group;

$R^8$, $R^9$ and $R^{10}$ are independently selected from the group consisting of hydrogen, a $C_1$-$C_{20}$ alkyl group, a $C_3$-$C_{20}$ alkenyl group, a $C_3$-$C_{20}$ alkynyl group, a $C_7$-$C_{20}$ arylalkyl group, —CN, —OR$^{12}$, —SR$^{12}$ and —N(R$^{12}$R$^{13}$), wherein $R^{12}$ and $R^{13}$ are independently selected from the group consisting of hydrogen, a $C_1$-$C_{20}$ alkyl group and a $C_6$-$C_{20}$ aryl group; wherein $R^8$ and $R^9$, $R^8$ and $R^{10}$ or $R^9$ and $R^{10}$ optionally form a ring structure, said ring structure optionally comprising a hetero-atom, said hetero-atom being selected from the group consisting of N, O, S, and an oxo group.

If $R^8$, $R^9$ or $R^{10}$ is a —N(R$^{12}$R$^{13}$) group it is preferred that $R^{12}$ and $R^{13}$ are not both hydrogen.

Preferably m=5-12, more preferably 5-10, even more preferably 5-8, most preferably 6-8.

$R^1$ is preferably hydrogen.

$R^2$ is preferably selected from the group consisting of a $C_6$-$C_{20}$ alkyl group, a $C_6$-$C_{20}$ alkenyl group, a $C_6$-$C_{20}$ alkynyl group, a $C_6$-$C_{20}$ aryl group and a group of the formula —$(CR^{18}_2)_o$N$(R^{17})CH_2R^3$, wherein o=3-9, each $R^{18}$ is independently selected from a hydrogen atom, a $C_1$-$C_6$ alkyl group or a $C_1$-$C_6$ alkoxy group and $R^3$ is $C_6$-$C_{20}$ alkyl group, a $C_6$-$C_{20}$ aryl group or a group of the formula —$(CR^{18}_2)_p$N$(R^{17})CH_2R^4$, wherein p=3-9, each $R^{18}$ is as defined above and $R^4$ is $C_6$-$C_{20}$ alkyl group, a $C_6$-$C_{20}$ aryl group or a group of the formula —(CR$^{18}_2$)$_q$N(R$^{17}$)CH$_2$R$^5$, wherein q=3-9, each R$^{18}$ is as defined above and R$^5$ is a C$_6$-C$_{20}$ alkyl group or a C$_6$-C$_{20}$ aryl group.

R$^8$, R$^9$ and R$^{10}$ are preferably hydrogen.

R$^{18}$ is preferably hydrogen.

R$^6$ and R$^7$ are preferably selected from the group consisting of —C(O)OR$^{11}$, —C(O)R$^{11}$ and —S(O$_2$)R$^{11}$, wherein R$^{11}$ is a C$_6$-C$_{20}$ aryl group or a C$_1$-C$_{25}$ alkyl group. More preferably R$^6$ is S(O$_2$)R$^{11}$, wherein R$^{11}$ is a C$_6$-C$_{20}$ aryl group, most preferably a C$_6$ aryl group. It is furthermore preferred that R$^7$ is C(O)OR$^{11}$, wherein R$^{11}$ is a C$_1$-C$_{25}$ alkyl group, more preferably a C$_1$-C$_{12}$ alkyl group, most preferably a C$_8$ alkyl group.

It is even more preferable that R$^2$ is a C$_6$-C$_{20}$ alkyl group, a C$_6$-C$_{20}$ alkenyl group, a C$_6$-C$_{20}$ alkynyl group or a C$_6$-C$_{20}$ aryl-group, more preferably a C$_6$-C$_{20}$ alkyl group or a C$_6$-C$_{20}$ aryl group, even more preferably a C$_6$-C$_{12}$ aryl-group, most preferably a C$_6$ aryl group.

Use of the UV-Absorbing Compounds

The present invention also relates to the use of the UV-absorbing compounds according to Formulas (VI), (VII) or (XI) for the protection of a mammal against UV-radiation, in particular to protection against UV-A-radiation.

The present invention further relates to compositions for protecting a mammal against UV-radiation, in particular against UV-A-radiation, comprising from about 0.01 to about 40. wt. %, preferably from about 0.5 to about 20 wt % and even more preferred from about 1.0 to about 10 wt. % of a UV-absorbing compound according to Formulas (VI), (VII) or (XI), based on the total weight of the composition.

These compositions according to the present invention may comprise other components that provide protection against either UV-A and/or UV-B-radiation.

Preferably these compositions comprise compounds of this invention as well as UV-B absorbing compounds and/or so-called broad-band UV absorbing compounds. Additionally these compositions may comprise other UV-A absorbing compounds such as the dibenzoylmethane derivative Parsol™ 1789.

Suitable components which can be additionally used with the UV-absorbers in these compositions according the present invention are any UV-A and UV-B filter substances like p-aminobenzoic acid derivatives, such as 4-dimethylaminobenzoic acid 2-ethylhexyl ester, benzophenone derivatives such as 2-hydroxy-4-methoxybenzophenone, salicylic acid derivatives such as salicylic acid 2-ethylhexyl ester, 3-imidazo-4-yl acrylic acid and esters, diphenylacrylates such as 2-ethylhexyl 2-cyano-3,3-diphenyl acrylate, polymeric UV-absorbers such as benzylidene malonate derivatives, benzofuran derivatives such as 2-(p-aminophenyl)benzofuran derivatives, camphor derivatives, for example 3-(4'-trimethylammonium)-benzylidene-bornan-2-one methyl sulphate, cinnamic acid derivatives such as 4-methoxycinnamic acid 2-ethylhexyl ester, hydroxyphenyltriazine UV-absorbers such as 2-(4'-methoxyphenyl)-4,6, (2'-hydroxy-4'-n-octylphenyl)-1,3,5-triazine, aminohydroxy-benzophenone derivatives such as disclosed in EP 1133980 and EP 1046391, phenyl-benzimidazole derivatives such as disclosed in EP 1167358, or the compounds as disclosed in Table 1, page 4 and Table 2 and 3, page 5 of DE 10331804, or the compounds such as examples 1-5 and 15 on pages 6-8 of EP 613893, or the compounds as disclosed in Table 1, pages 18-21 of EP 1000950, or the compounds as disclosed in Table 3, page 13 of EP 1005855, or the compounds as disclosed in examples 1-3 on pages 13-15 of EP 1008586, or the compounds as disclosed in examples 1-8 on pages 4-5 of EP 1008593, or the compounds I-VII as disclosed on page 3 of EP 1027883, or the compounds as disclosed in examples 1-5 on pages 5-13 of EP 1028120, or a the compound as disclosed in example 1 and Table 1 on pages 9-11 of EP 1059082, or compounds as disclosed in Tables 1-3 on pages 11-14 of EP 1060734, or compounds 1-34 as disclosed on pages 6-14 of EP 1064922, or compounds as disclosed in examples 1-9 on pages 11-16 of EP 1081140, or compounds 1-76 as disclosed on pages 39-51 of EP 1103549, or the compound 4,5-dimorpholino-3-hydroxypyridazine as disclosed in EP 1108712, or the compounds disclosed in Table 3 on page 10 of EP 1123934, or the compounds as disclosed in examples 1-7 on pages 13-14 of EP 1129695, or the compounds as disclosed in examples 1-2 on pages 11 and 12 of EP 1167359, or the compound as disclosed in example 1 on page 7 of EP 1258481, or the compound as disclosed in example 3 on page 13 of EP 420707, or the compounds as disclosed in Table 1 on pages 9-10 of EP 503338, or the compounds as disclosed in examples 3, 4, 9 and 10 on pages 6-7 of EP 517103, or the compounds as disclosed in examples 1 and 8 as on pages 4-8 in Table 1 and 2 of EP 517104, all compounds as disclosed in EP 626950, or the compounds as disclosed in examples 1-3 on page 5 of EP 669323, or the compounds as disclosed in examples 1-11 on pages 1-11 of EP 780823, or the compounds as disclosed in examples 1-4 on pages 7-8 of EP 823418, or the compounds as disclosed in Table 1 on pages 5-6 of EP 826361, or the compounds as disclosed in examples 5 and 6 on pages 7-8 of EP 823641, the compounds as disclosed example 22 on pages 10-16 of EP 832642, or the compounds as disclosed in Table 2 on pages 41-46 of EP 852137, or the compounds as disclosed in Table 1 on page 6 of EP 858318, or the compounds as disclosed in examples 1-11 on pages 12-18 of EP 863145, or the compounds as disclosed in Table 2 on pages 11-12 of EP 911020, or the compounds as disclosed in Tables 2-4 on pages 19-41 of EP 916335, or the compounds as disclosed in Table 2 of EP 924246, or the compounds as disclosed in examples 1-15 on pages 10-21 of EP 933376, or the compounds as disclosed in examples 1 and 2 on pages 13-15 of EP 944624, or the compounds a and b as disclosed in Table 3 on pages 14-15 of EP 945125, or the compounds as disclosed in Tables 3-5 on pages 17-20 of EP 967200, or the compounds as disclosed in example 5 and in Table 1 on pages 6-8 of EP 969005, all compounds disclosed on pages 5-10 of U.S. Pat. No. 5,635, 343, or the compounds as disclosed in examples 1-9 on pages 3-4 of U.S. Pat. No. 5,338,539, or the compounds such as disclosed in example 40 on page 7 or as disclosed in Table 5 on page 8 of U.S. Pat. No. 5,346,691, or the compounds as disclosed in examples 1-5 on pages 6-7 of U.S. Pat. No. 5,801,244, or the compounds as disclosed in examples 1-5 on pages 16-21 of WO 0149686, or the compounds as disclosed in the tables on pages 85-96 of WO 0168047, or the compounds such as disclosed in examples 1-3 on pages 9-11 of WO 0181297, or the compounds as disclosed in Table MC2a on pages 10-26 of WO 06003094, or the compounds such as disclosed on pages 3 and 4 of WO 0238537, or the compounds as disclosed in examples 1-22 on pages 10-20 of WO 9217461, or the compounds as disclosed in Table 1 on pages 3-5 in WO 07071582, or the compounds as disclosed in Table MC1 on pages 8-15 of WO 05058269, or the compounds as disclosed in examples 3-6 of WO 9220690, or the compounds as disclosed in Tables 1-2 on pages 13-22 of WO 9301164, or the compounds as disclosed in examples 1-3 on page 10 of WO 9714680.

Very suitable to be used additionally in the compositions with the UV-absorbers according to the present invention are the following compounds:

1,7,7-trimethyl-3-[phenylmethylene]bicyclo[2.2.1]heptan-2-one;
1,7,7-trimethyl-3-[(4-methylphenyl)methylene]bicyclo[2.2.1]heptan-2-one;
(2-hydroxy-4-methoxyphenyl)(4-methylphenyl)methanone;
2,4-dihydroxybenzophenone;
2,2',4,4'-tetrahydroxybenzophenone;
2-hydroxy-4-methoxybenzophenone;
2-hydroxy-4-methoxybenzophenone-5-sulfonic acid;
2,2'-dihydroxy-4,4'-dimethoxybenzophenone;
2,2'-dihydroxy-4-methoxybenzophenone;
alpha-(2-oxoborn-3-ylidene)toluene-4-sulfonic acid and its salts;
1-[4-(1,1-dimethylethyl)phenyl]-3-(4-methoxyphenyl)propane-1,3-dione (commercially known under the name Parsol™ 1789);
methyl-N,N,N-trimethyl-4-[(4,7,7-trimethyl-3-oxobicyclo[2.2.1]hept-2-ylidene)methyl]anilinium sulphate;
3,3,5-trimethyl-cyclohexyl-2-hydroxy-benzoate; isopentyl p-methoxycinnamate;
menthyl o-aminobenzoate;
menthyl salicylate;
2-ethylhexyl 2-cyano-3,3-diphenylacrylate;
2-ethylhexyl 4-(dimethylamino)benzoate;
ethylhexyl 4-methoxycinnamate;
ethylhexyl salicylate;
benzoic acid;
4,4',4"-(1,3,5-triazine-2,4,6-triyltriimino)tris,tris(2-ethylhexyl)ester;
2,4,6-trianilino-(p-carbo-2'-ethylhexyl-1'-oxy)-1,3,5-triazine;
4-aminobenzoic acid;
benzoic acid, 4-amino-,ethyl ester, polymer with oxirane;
2-phenyl-1H-benzimizadole-5-sulphonic acid;
triethanolamine salicylate;
3,3'-(1,4-phenylenedimethylene)bis[7,7-dimethyl-2-oxo-bicyclo[2.2.1]heptane-1-methanesulphonic acid];
titaniumdioxide;
zinc oxide;
2,2'-methylene-bis[(6-(2H-benzotriazol-2-yl)-4-(1,1,3,3-tetramethyl-butyl)-phenol];
2,4-bis{[4-(2-ethylhexyloxy)-2-hydroxy]-phenyl}-6-(4-methoxy-phenyl)-1,3,5-triazine;
benzoic acid, 4,4"-[[6-[[4-[[(1,1-dimethylethyl)amino]carbonyl]phenyl]amino]1,3,5-triazine-2,4-diyl]diimino]bis-,bis(2-ethylhexyl) ester;
phenol, 2-(2H-benzotriazol-2-yl)-4-methyl-6-[2-methyl-3-[1,3,3,3-tetramethyl-1-[(trimethylsilyl)oxy]siloxanyl]propyl];
dimethicodiethylbenzalmalonate;
benzenesulphonic acid, 3-(2H-benzotriazol-2-yl)-4-hydroxy-5-(1-methylpropyl)-monosodium salt;
benzoic acid, 2-[4-(diethylamino)-2-hydroxybenzoyl]-, hexyl ester;
1-dodecanaminium, N-[3-[[4-dimethylamino)benzoyl]amino]propyl]-N,N-dimethyl, salt with 4-methylbenzenesulphonic acid 1:1;
1-propanaminium,N,N,N-trimethyl-3-[(1-oxo-3-phenyl-2-propenyl)-amino]-, chloride;
1H-benzimidazole-4,6-disulphonic acid, 2,2'-(1,4-phenylene)bis-;
1,3,5-triazine, 2,4,6-tris(4-methoxyphenyl)-;
1,3,5-triazine, 2,4,6-tris[4-(2-ethylhexyl)oxy]phenyl]-;
1-propanaminium,3-[[3-[3-(2H-benzotriazol-2-yl)-5-(1,1-dimethylethyl)-4-hydroxyphenyl]-1-oxopropyl]amino]-N,N-diethyl-N-methyl-, methyl sulphate (salt);
2-propenoic acid, 3-(1H-imidazol-4-yl)-;
benzoic acid, 2-hydroxy-,[4-(1-methylethyl)phenyl]methyl ester;
1,2,3-propanetriol, 1-(4-aminobenzoate);
benzene acetic acid, 3,4-dimethoxy-alpha-oxo;
2-propenoic acid, 2-cyano-3,3-diphenyl-,ethyl ester;
anthranilic acid, p-menth-3-yl ester;
2,2'-bis(1,4-phenylene)-1H-benzimidazole-4,6-disulphonic acid monosodium salt or disodium phenyl dibenzimidazole tretrasulphonate.

Most preferably, the compounds of this invention are mixed with other UV-absorbers to obtain full protection against UV-light. Particularly combinations with one or more UV-B and/or broadband absorbers are beneficial to provide full spectrum UV-protection. Also combination with one or more UV-A absorbers is beneficial to reduce the concentration of each UV-A absorber and hence reduce possible detrimental health effects. These UV-absorbers may be organic or physical sunscreens. The most preferred UV-absorbers are chosen from the approved UV-absorbers for cosmetic use as exemplified by the cosmetics directive 76/786/EEC of the European Community. These examples include: 4-aminobenzoic acid (PABA), N,N,N-trimethyl-4-(2-oxoborn-3-ylidene-methyl) anilinium methyl sulphate (CBM, Mexoryl™ SK), homosalate (HMS), oxybenzone (BENZ-3, Uvinul™ M40), 2-phenylbenzimidazole-5-sulphonic acid and its potassium, sodium and triethanolamine salts (PBSA, Neo Heliopan™ Hydro), 3,3'-(1,4-phenylenedimethylene)-bis-(7,7-dimethyl-2-oxo-bicyclo-[2,2,1]-hept-1-ylmethane-sulphonic acid) and its salts (TDSA, Mexoryl™ SX), 1-(4-tert-butylphenyl)-3-(4-methoxyphenyl)propane-1,3-dione (BMDBM, Parsol™ 1789, alpha-(2-oxoborn-3-ylidene) toluene-4-sulphonic acid and its salts (BCSA, Mexoryl™ SD-20, 2-cyano-3,3-diphenyl acrylic acid, 2-ethyl hexyl ester (OC, Octocrylene, Eusolex™ OCR), Polymer of N-{(2 and 4)[2-oxoborn-3-ylidene)methyl]benzyl}acrylamide (PBC, Mexoryl™ SW), octyl methoxycinnamate (OMC, Parsol™ MCX), ethoxylated ethyl-4-amino-benzoate (PEG-PABA, Uvinul™ P25), isopentyl-4-methoxycinnamate or isoamyl p-methoxycinnamate (IMC, Neo Heliopan™ E1000), 2,4,6-trianilino-(p-carbo-2'-ethylhexyl-1'-oxy)-1,3,5-triazine (octyl triazone, ET, Uvinul™ T150), pheno-1,2-(2H-benzotriazol-2-yl)-4-methyl-6-(2-methyl-3-(1,3,3,3-tetramethyl-1-(trimethyl-silyl)oxy)-disiloxanyl)propyl) (or drometrizole trisiloxane, DTS, Mexoryl™ XL), Benzoic acid 4,4-((6-(((1,1-dimethylethyl)amino carbonyl)phenylamino-1,3,5-triazine-2,4-diyl)diimino)-bis-bis-(2-ethylhexyl)ester) (DBT, Uvasorb™ HEB), 3-(4'-methylbenzyl-idene)-d-1 camphor (or 4-methylbenzylidene camphor) (MBC, Uvinul™ MBC95), 3-benzylidene camphor (BC, mexoryl-SD20), 2-ethylhexyl salicylate (ES, octyl-salicylate), 4-dimethylamino-benzoate of ethyl-2-hexyl (or octyl dimethyl PABA, ED-PABA), 2-hydroxy-4-methoxybenzophenone-5-sulphonic acid (benz-4, Uvinul™ MS 40) and its sodium salt (benz-5), 2,2'-methylene-bis-6(2H-benzotriazole-2-yl)-4-(tetramethyl-butyl)-1,1,3,3-phenol (MBBT, Tinosorb™ M), monosodium salt of 2,2'-bis-(1,4-phenylene) 1H-benzimidazole-4,6-disulphonic acid (DPDT, Neoheliopan™ AP), (1,3,5)-triazine-2,4-bis((4-(2-ethyl-hexyloxy)-2-hydroxy)-phenyl)-6-(4-methoxyphenyl) (BEMT, Tinosorb™ S), dimethicodiethylbenzalmalonate (DDBM, Parsol™ SLX), titanium dioxide (TiO), zinc oxide (ZnO).

Other suitable compounds are those approved for use in the United States: 2-ethoxyethyl p-methoxycinnamate (Cinoxate™), triethanolamine salicylate and benzophenone-8.

Preferably the compound of the invention is used in a composition with UV-B and/or broadband UV absorbers in a weight ratio of between 1:10 and 10:1, more preferably between 1:6 and 4:1. Below a ratio of 1:10 the additional effect is considered to be too small and above a ratio of 10:1 the protection against UV-B radiation is in most applications insufficient.

Preferably the composition comprises between 1 weight % and 10 weight % of the compound of the invention and up to 70 weight % of oil, preferably alkyl benzoate oil, e.g. about 50 weight % of oil. For an optimal effectiveness the ratio of UV absorbing compound according the invention and oil is preferably higher than 0.05, more preferably higher than 0.1.

Table 1 provides examples of suitable combinations of the compounds of the invention with commercially available UV-absorbers mentioned above.

The content is expressed as weigh percent, based on the total weight of a formulation. A particular suitable compound for use in the combinations listed in Table 1 is compound 4 according to the present invention (described in inventive example 1) and exemplified in table 2.

These compositions according to the invention may also contain one or more additional compounds like fatty alcohols or esters of fatty acids, natural or synthetic triglycerides including glyceryl esters and derivatives, pearlescent waxes, hydrocarbon or alkyl benzoate oils preferably $C_{12}$-$C_{15}$ alkyl benzoate oils, silicones or siloxanes, organo-substituted superfatting agents (Handmade soap differs from industrial soap in that, usually, an excess of fat is used to consume the alkali (superfatting), and in that the glycerine is not removed. Superfatted soap, soap which contains excess fat, is more skin-friendly than industrial soap), surfactant-consistency regulators or thickeners, deodorising active ingredients, antidandruff agents, antioxidants, hydrotropic agents, preservatives and bacteria-inhibiting agents, perfume oils, colorants, polymeric beads or hollow spheres.

TABLE 1

Examples of suitable combinations of UV absorbers

| Compound A | Content (wt %) | Compound B | Content (wt %) | Compound C | Content (wt %) |
|---|---|---|---|---|---|
| Invention | 2% | OMC | 10% | | |
| Invention | 4% | OMC | 5% | | |
| Invention | 6% | OMC | 2% | | |
| Invention | 1% | OMC | 5% | BMDBM | 1% |
| Invention | 2% | OMC | 3% | BMDBM | 1% |
| Invention | 2% | OMC | 3% | BMDBM | 2% |
| Invention | 1% | ET | 1% | | |
| Invention | 3% | ET | 3% | | |
| Invention | 2% | ET | 1% | BMDBM | 2% |
| Invention | 1% | BEMT | 1% | | |
| Invention | 4% | BEMT | 3% | | |
| Invention | 2% | BEMT | 1% | BMDBM | 2% |
| Invention | 2% | DBT | 1% | | |
| Invention | 2% | DBT | 3% | | |
| Invention | 2% | DBT | 1% | BMDBM | 2% |
| Invention | 1% | DTS | 1% | | |
| Invention | 4% | DTS | 3% | | |
| Invention | 2% | DTS | 1% | BMDBM | 2% |
| Invention | 1% | MBBT | 1% | | |
| Invention | 4% | MBBT | 3% | | |
| Invention | 2% | MBBT | 1% | BMDBM | 2% |
| Invention | 2% | DDBM | 2% | | |
| Invention | 2% | DDBM | 2% | BMDBM | 2% |
| Invention | 2% | DPDT | 2% | | |
| Invention | 1% | DPDT | 3% | BEMT | 2% |
| Invention | 1% | ES | 1% | | |
| Invention | 3% | ES | 2% | | |
| Invention | 3% | ES | 2% | BMDBM | 2% |
| Invention | 1% | PABA | 1% | | |
| Invention | 3% | PABA | 2% | | |
| Invention | 3% | PABA | 2% | BMDBM | 2% |

TABLE 1-continued

Examples of suitable combinations of UV absorbers

| Compound A | Content (wt %) | Compound B | Content (wt %) | Compound C | Content (wt %) |
|---|---|---|---|---|---|
| Invention | 1% | CBM | 1% | | |
| Invention | 3% | CBM | 2% | | |
| Invention | 3% | CBM | 2% | BMDBM | 2% |
| Invention | 1% | HMS | 1% | | |
| Invention | 3% | HMS | 2% | | |
| Invention | 3% | HMS | 2% | BMDBM | 2% |
| Invention | 1% | TiO | 5% | | |
| Invention | 3% | TiO | 10% | | |
| Invention | 3% | TiO | 5% | BMDBM | 2% |
| Invention | 1% | ZnO | 5% | | |
| Invention | 3% | ZnO | 10% | | |
| Invention | 3% | ZnO | 5% | BMDBM | 2% |

TABLE 2

Specific examples of suitable combinations of UV absorbers

| Compound A | Content (wt %) | Compound B | Content (wt %) | Compound C | Content (wt %) |
|---|---|---|---|---|---|
| Compound 4 | 2% | OMC | 10% | | |
| Compound 4 | 4% | OMC | 5% | | |
| Compound 4 | 6% | OMC | 2% | | |
| Compound 4 | 1% | OMC | 5% | BMDBM | 1% |
| Compound 4 | 2% | OMC | 3% | BMDBM | 1% |
| Compound 4 | 2% | OMC | 3% | BMDBM | 2% |
| Compound 7 | 2% | OMC | 3% | BMDBM | 2% |
| Compound 8 | 2% | OMC | 3% | BMDBM | 2% |
| Compound 4 | 1% | ET | 1% | | |
| Compound 4 | 3% | ET | 3% | | |
| Compound 4 | 2% | ET | 1% | BMDBM | 2% |
| Compound 4 | 1% | BEMT | 1% | | |
| Compound 4 | 4% | BEMT | 3% | | |
| Compound 4 | 2% | BEMT | 1% | BMDBM | 2% |
| Compound 4 | 2% | DBT | 1% | | |
| Compound 4 | 2% | DBT | 3% | | |
| Compound 4 | 2% | DBT | 1% | BMDBM | 2% |
| Compound 4 | 1% | DTS | 1% | | |
| Compound 4 | 4% | DTS | 3% | | |
| Compound 4 | 2% | DTS | 1% | BMDBM | 2% |
| Compound 4 | 1% | MBBT | 1% | | |
| Compound 4 | 4% | MBBT | 3% | | |
| Compound 4 | 2% | MBBT | 1% | BMDBM | 2% |
| Compound 4 | 2% | DDBM | 2% | | |
| Compound 4 | 2% | DDBM | 2% | BMDBM | 2% |
| Compound 4 | 2% | DPDT | 2% | | |
| Compound 4 | 1% | DPDT | 3% | BEMT | 2% |
| Compound 4 | 1% | ES | 1% | | |
| Compound 4 | 3% | ES | 2% | | |
| Compound 4 | 3% | ES | 2% | BMDBM | 2% |
| Compound 4 | 1% | PABA | 1% | | |
| Compound 4 | 3% | PABA | 2% | | |
| Compound 4 | 3% | PABA | 2% | BMDBM | 2% |
| Compound 4 | 1% | CBM | 1% | | |
| Compound 4 | 3% | CBM | 2% | | |
| Compound 4 | 3% | CBM | 2% | BMDBM | 2% |
| Compound 4 | 1% | HMS | 1% | | |
| Compound 4 | 3% | HMS | 2% | | |
| Compound 4 | 3% | HMS | 2% | BMDBM | 2% |
| Compound 4 | 1% | TiO | 5% | | |
| Compound 4 | 3% | TiO | 10% | | |
| Compound 4 | 3% | TiO | 5% | BMDBM | 2% |
| Compound 4 | 1% | ZnO | 5% | | |
| Compound 4 | 3% | ZnO | 10% | | |
| Compound 4 | 3% | ZnO | 5% | BMDBM | 2% |
| Compound 7 | 3% | ZnO | 5% | BMDBM | 2% |
| Compound 8 | 3% | ZnO | 5% | BMDBM | 2% |

Compound 4 is the reaction product of the n-octyl ester of N,N-(phenylsulfonyl, carboxyl)-aminobutadiene and $N^1$-benzyl-$N^6$-(6-(benzylamino)hexyl)hexane-1,6-diamine The compositions according to the present inventions may exist in a wide variety of presentation forms, for example in the form of liquid preparations as alcoholic or aqueous/alcoholic solutions or water- and oil containing emulsions (e.g. W/O-, O/W-, O/W/O-, W/O/W-emulsions and all kind of micro-emulsions), in the form of a gel or in the form of an oil, a cream or lotion or in the form of a powder, lacquer, tablet or make-up, in the form of a stick, or in the form of a spray, or foam or a paste or ointment.

Of special importance as compositions for the skin are light-protective compositions, such as sun milks, lotions, creams, oils, sun-blocks or topicals, after-sun compositions and skin-tanning compositions. Of particular interest are sun protection creams, sun protection lotions, sun protection milk and sun protection compositions in the form of a spray.

EXAMPLES

Inventive Example 1

Preparation of Compound 4

Compound 4 was prepared according to the synthesis shown below:

All solvents used were purchased from Sigma-Aldrich. The solvents were at least synthetic grade and used without further treatment.

Step 1: Preparation of Compound 2, di-benzyl BHMTA

Amine 1 ($N^1$-benzyl-$N^6$-(6-(benzylamino)hexyl)hexane-1,6-diamine=BHMTA (bishexamethylene triamine), Sigma Aldrich, high purity), was distilled in vacuum (164 degrees celcius, 4 mm Hg) before usage (yield >95%, purity >99%). Purified amine 1 (50 g, 232 mmol) was dissolved in 2-propanol (IPA, 300 ml) and cooled to 0° C. Hereafter, benzaldehyde (Acros Organics, 98+%, 49.3 g, 465 mmol) was added dropwise. The solution was warmed to 20° C. and stirred for 2 hours. Then a catalytic amount—(10 mol % versus the amine 1) of Pd/C (Palladium on activated carbon unreduced 10% Pd, Acros Organics) was added and the solution was stirred under 2 bar $H_2$ (g) atmosphere for 16 hours. The solution was then filtered (through Celite-535 coarse Fluka) to remove the Pd/C and was evaporated until dryness to yield compound 2. Yield and purity were excellent, but compound 2 was also purified by HCl salt formation in ethyl acetate (80 g/1.3 L) with HCl (g), filtered, washed on the filter with ethyl acetate and liberated with NaOH in toluene. Yield is 61%.

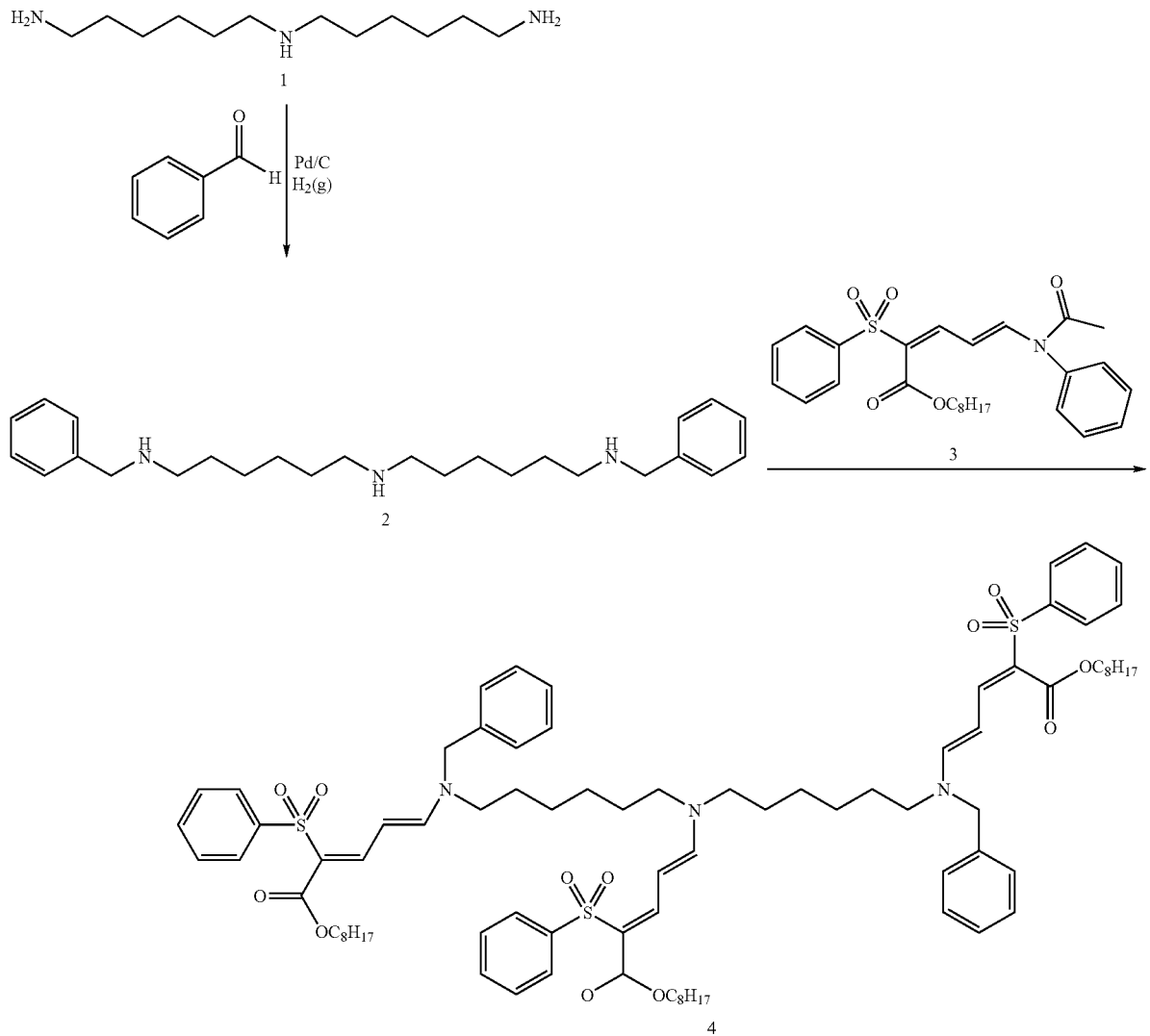

Step 1a: Preparation of Aminobutadiene 3

Aminobutadiene 3 was prepared according to the following procedure: 1-anilino-3-phenyliminopropene (100 g, 0.45 mol, Aldrich, >99%), n-octyl phenyl sulphonyl acetate (141 g), and N,N-diisopropylethylamine (36.6 ml, 0.22 mol) were dissolved in acetonitril (100 ml). Then 98 ml acetic anhydride (Aldrich, >99%) was added while stirring. Subsequently the mixture was heated for 2 hours at 80° C. Aminobutadiene 3 was precipitated by adding subsequently 200 ml iso-propanol and 400 ml water. Aminobutadiene 3 was isolated by filtration and washed 3 times with 100 ml isopropanol. After drying under reduced pressure aminobutadiene 3 was obtained in 80% yield and a purity of >98%, but alsp the crude aminobutadiene 3 was re-crystallised from ethylacetate/heptane (1:1 volume ratio).

Step 2: Coupling to Aminobutadiene 3

Compound 2 (54.5 g, 138 mmol) and aminobutadiene 3 (200 g, 414 mmol) were stirred in IPA (400 ml) for 16 hours at reflux. Upon cooling to room temperature and the addition of water pahae separation occurred. The solvent was decanted and the oil containing the product, compound 4, was dissolved in IPA (800 ml) at 60° C. This procedure was repeated two times until all acetanilide has been removed. Finally the material was evaporated until dryness.

Alternatively, compound 2 (54.5 g, 138 mmol) and aminobutadiene 3 (200 g, 414 mmol) and sodium acetate (Aldrich, 9.35 g, 68.7 mmol) were stirred in IPA (400 ml) and sodium phosphate buffer (100 ml, 0.5 M, pH 6.8) for 16 hours at reflux. Upon cooling to room temperature, and the addition of seed crystals complete crystallization occurred within several hours. Then an additional amount of water (1.5 L) was added. After filtration the yellow solids were stirred in methanol (1.5 L). This procedure was repeated 2 times yielding compound 4 in 70% yield with a purity of 98%, (extinction E=1400 au/cm for a 1% solution in DMSO at 375 nm).

Purification Method 1

Compound 4 thus obtained was further purified by column chromatography on a silica column (1 g of compound/50 g silica) using ethyl acetate/hexane in 1/1 volume ratio as first eluent to elute the impurities and pure ethyl acetate as second eluent to elute the target compound. After evaporating the solvent, compound 4 was obtained in 50% yield with a purity on HPLC>98%.

Purification Method 2

In an alternative method for the purification of compound 4, the crude product was dissolved in a minimal amount acetone/methanol 1/1 volume ratio at room temperature. The temperature was lowered to −5° C. while stirring. After 16 hours the formed solid was collected by filtration and washed on the filter with cold methanol. After drying in vacuo at room temperature, compound 4 was obtained in 70% yield with a purity on HPLC>98%.

Comparative Example 1

Coupling of Aminobutadiene 3 to BHMTA

Amine 1 (54.5 g, 138 mmol) and aminobutadiene 3 (200 g, 414 mmol) were stirred in IPA (400 ml) for 16 h at reflux. After cooling to room temperature water was added to speed up phase separation. Then the solvent was decanted and the remaining oil was dissolved in IPA (800 ml) at 60° C. This procedure was repeated two times until all acetanilide was removed. The solution was evaporated until dryness yielding compound 5. Purification by column chromatography as described above for compound 4. Yield: 52%, purity >97%. The resulting compound 5 contains 2 aminobutadiene units which are coupled via a secondary nitrogen atom to the core.

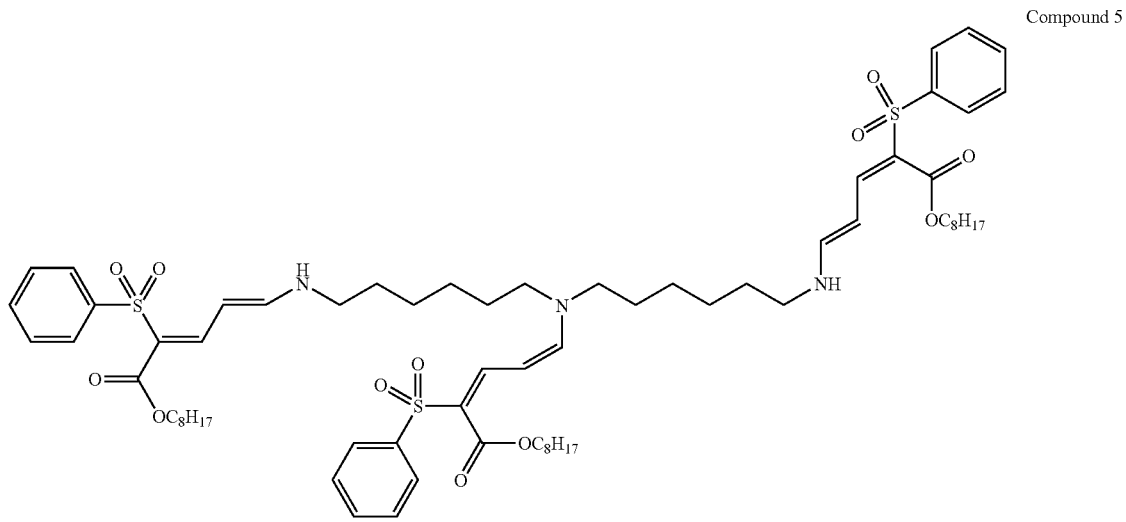

Compound 5

Inventive Example 2

Preparation of Compound 6

Compound 6 was prepared according to the method of Example 1, provided that butyraldehyde (Sigma-Aldrich, 99%, dry) was used in stead of benzylaldehyde. After reaction with aminobutadiene 3 and purification by column chromatography as described for compound 4, compound 6 was obtained in a yield of 45%, purity 96%.

Inventive Example 3

Preparation of Compound 7

Instead of bishexamethylene triamine (BHMTA), tris(2-aminoethyl)amine (Acros, 96%, TREN) was used. The benzylaldehyde derivative was prepared according to method described in Example 1. After reaction with aminobutadiene 3 and purification by column chromatography as described for compound 4, compound 7 was obtained with a yield of 48%, purity >97%

Inventive Example 4

Preparation of Compound 8

Instead of BHMTA, diaminobutane derivate DAB4=Astramol Am(4) (DSM) was used. The benzylaldehyde derivative was prepared according to method described in Example 1. After reaction with aminobutadiene 3 and purification by column chromatography as described for compound 4, compound 8 was obtained with a yield of 55%, purity >97%.

Inventive Example 5

Preparation of Compound 9

Instead of BHMTA diethylenetriamine (98.5% Acros) was used in combination with benzylaldehyde. The coupling of aminobutadiene 3 with the benzylaldehyde derivative of diethylenetriamine yielded the target compound 9 in a raw yield of 45%. After purification by column chromatography as described in purification method 1 the yield was 35%, purity >97%.

Comparative Example 2

Coupling of Aminobutadiene 3 to TREN

Instead of BHMTA, triaminoethylamine (TREN) was used. The compound was prepared according to the method described in Comparative Example 1, yielding compound 10 with a yield of 48%, purity >97%.

Comparative Example 3

Coupling of Aminobutadiene 3 to DAB4

Instead of BHMTA, DAB4=Astramol Am(4) was used. The compound was prepared according to the method described in Comparative Example 1, yielding compound 11 with a yield of 60%, purity 96%.

Comparative Example 4

Aminobutadiene Coupled to Gelatine

Aminobutadiene coupled to gelatine was prepared according to the method described in WO 2004/075871. The UV-A absorbing gelatine (UV-A-gel, compound 12) thus prepared has an extinction value E=380 au/cm for a 1% solution in water at 375 nm).

Inventive Example 6

Instead of BHMTA diethylenetriamine (98.5% Acros) was used in combination with butyraldehyde. The coupling of aminobutadiene 3 with the butyraldehyde derivative of diethylenetriamine yielded the target compound 13 in a raw yield of 40%. After purification by column chromatography as described in purification method 1 the yield was 21%, purity >97%.

Inventive Examples 7-9

Aminobutadienes 14, 15 and 16 were prepared by the procedure described for aminobutadiene 3 in example 1 using respectively isopropyl phenyl sulphonyl acetate, ethyl-hexyl phenyl sulphonyl acetate, and stearyl phenyl sulphonyl acetate. Aminobutadienes 14, 15 and 16 were subsequently coupled to BHMTA as described in example 1. Work-up procedures were adapted depending on the compound. As such target compounds 17, 18, 19 were obtained in yields of 40-60% and purity of >97%

Spectral Analysis

The aminobutadiene compounds according to the present invention have a typical extinction value E of about 1100 to about 1500 AU/cm of a 1% solution in dimethylsulfoxide (DMSO, Sigma Aldrich ACS spectrophotometric grade) at 375 nm, which is typically the wavelength of the absorption maximum of such compounds. The exact value of E depends on the relative contribution of the core and the R-groups to the molecular weight, while the exact wavelength of the absorption maximum depends on the type of substituents. Spectra were obtained on a HP 8452A diode array spectrophotometer against a DMSO blanc. A representative UV-spectrum is given in FIG. 1.

Solubility Test

The aminobutadiene compounds according to the present invention have an optimised solubility for cosmetic oils. The preferred compound 4 is very well soluble at all concentrations in $C_{12}$-$C_{15}$ alkyl benzoate oil (Finsolv TN, Finetex) to give a clear viscous oil. In Table 3, the solubility of compounds 4, 12 and 13 is shown at various concentrations (+=well-soluble; –=not soluble). The compounds were dissolved at 80° C. while stirring for 1 hour and cooled down to room temperature. After 24 hours the solutions were inspected for any precipitates or crystals.

TABLE 3

Solubility of several compounds in Finsolv ™ TN at various concentrations

| | Dissolved amount (m/m %) | | | | | |
|---|---|---|---|---|---|---|
| | 1% | 5% | 20% | 50% | 80% | 90% |
| Compound 4 (invention) | + | + | + | + | + | + |
| Compound 12 UV-A-gel (comparative) | – | – | – | – | – | – |
| Compound 13 (invention) | + | + | + | – | – | – |
| Compound 17 (invention) | – | – | – | – | – | – |
| Compound 18 (Invention) | + | – | – | – | – | – |
| Compound 19 (Invention) | + | + | + | + | + | + |

Heat Stability Test

Hereto, 1.5% solutions were prepared of compounds 4-11 and 13 in $C_{12}$-$C_{15}$ alkyl benzoate oil. The UV-A-gel (compound 12) was dissolved at 5% in water (in order to have a comparable UV-absorption a higher concentration was chosen). The solutions were stored in closed vessels at 50° C. in the dark. After 5, 50 and 100 days, the UV-absorption of a diluted sample was measured at 375 nm comparative to a corresponding sample stored at room temperature. The UV-absorption left after each time span is shown in Table 4 indicated by + and − signs. ++ means >95% left, +− implies between 50-95% left, − indicates <50% left.

From the data it appears that compounds 4, 6, 7, 8, 9 and 13 having tertiary nitrogen atoms are very heat stable in $C_{12}$-$C_{15}$ alkylbenzoate oils compared to compounds 5, 10 and 11 having two or more secondary nitrogen atoms and even more when they are compared to compound 12a water-soluble aminobutadiene coupled to gelatin.

Although showing a good heat stability compounds 9 and 13 are less preferred because of the low synthesis yields.

TABLE 4

Heat stability in time of several compounds

| Compound | 5 days | 50 days | 100 days |
|---|---|---|---|
| 4 Invention | ++ | ++ | ++ |
| 5 Comparative | ++ | +− | +− |
| 6 Invention | ++ | ++ | ++ |
| 7 Invention | ++ | ++ | ++ |
| 8 Invention | ++ | ++ | ++ |
| 9 Invention | ++ | ++ | ++ |
| 10 Comparative | ++ | +− | − |
| 11 Comparative | ++ | +− | − |
| 12 Comparative (UV-A-gel) | +− | −− | −− |
| 13 Invention | ++ | ++ | ++ |
| 17 Invention | ++ | ++ | ++ |
| 18 Invention | ++ | ++ | ++ |
| 19 Invention | ++ | ++ | ++ |

Skin Penetration

Figure 2:
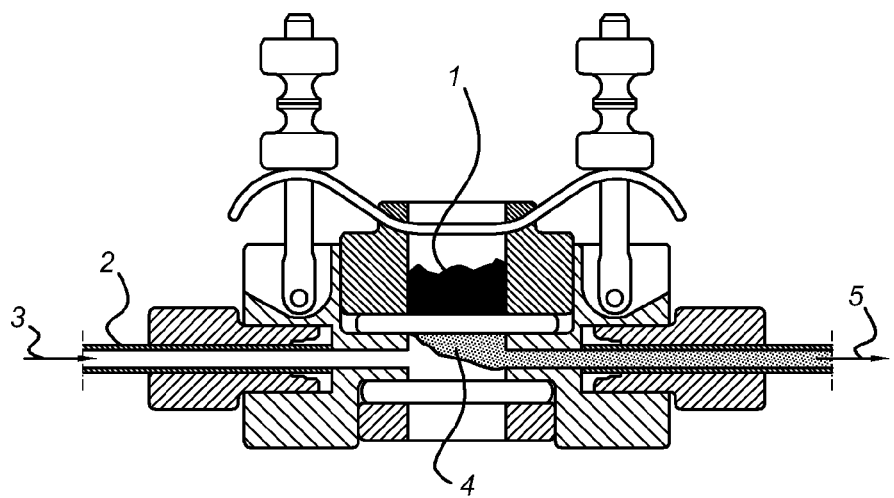
FIG. 2 is a drawing of the skin penetration test equipment.

The skin-penetration was evaluated based on the same method described on page 21 of WO2006/009451. FIG. 2 is a drawing of the skin penetration test equipment, wherein (1) indicates the position of the test sample (donor compound), (2) an ⅛" OD×1/32" wall tubing, (3) the receptor input, (4) the receptor compartment and (5) the compound and receptor output that is subjected to analysis.

A compound 3 donor solution was prepared by dissolving 30 mg of compound 3 in 4 ml EtOH and 7 ml phosphate buffer (PBS) at pH 7.4. Compound 4, 6, 7, 8 and 9 donor solutions were prepared by dispersing 80 mg of these compounds in olive oil.

For each compound 4 pieces of human skin (Ø ca 3 cm, mostly epidermis) were applied on a dialysis membrane and mounted into the diffusion cell shown in the FIG. 2. The figure is a schematic drawing of the diffusion cell, wherein is indicated 1: donor compound, 2: receptor compartment, 3: receptor input, 4: compound and receptor output for analysis, 5: ⅛" OD×1/32" wall tubing. The cells were mounted on a temperature controlling and stirring device. The temperature was kept at 37°. The receptor fluid was a PBS buffer. The receptor compartment was stirred magnetically. 400 µl of the donor solution was applied. The receptor fluid flowing at a speed of 1 ml/hr was collected into glass tubes (1 tube/2 hrs). After 20 hrs the penetration experiment was terminated.

UV-analysis of the collected receptor fluids indicated clearly the penetration of the UV-monomer compound 3 through the skin while no penetration was measured for the UV-compounds 4, 6, 7, 8 and 9 (see table 5 below).

Furthermore the skin parts were extracted with DMSO to dissolve any UV-absorber in the epidermis. The extracts were analysed by UV. The results, shown in table 5 second column, support the conclusion from the receptor fluids that the UV-compounds 4, 6, 7, 8 and 9 do not penetrate into or through the skin while the UV-monomer could be observed inside the skin sample.

TABLE 5

Results of skin penetration test for several compounds

| Compound | Presence in receptor fluid after 6 h | Presence in skin extract |
|---|---|---|
| aminobutadiene 3 | + | + |
| compound 4, 6, 7, 8, 9 | − | − |

In Table 5, a '+' means that more than 50% of the substance penetrates the skin; a '−' means that no detectable amount of the substance penetrated the skin (less than 5%) and '+/−' would mean that between 5% and 50% of the substance penetrates the skin.

Light Stability

Combination of various UV-absorbers (UV-A+UV-B) is desired to create a complete UV protection but also serves to protect certain UV-absorbers from light fading. In the past this effect has been demonstrated especially for 1-(4-tert-butylphenyl)-3-(4-methoxyphenyl)propane-1,3-dione (BM-DBM, Parsol™ 1789) which was shown to be stabilised by several other UV-absorbers. In this example it is shown that combination of compound 4 with broadband UV absorbers like ET and UV-B absorbers like OMC has excellent light stability. Further addition of BMDBM to these also showed good light stability. All tested combinations showed satisfactory results. Results are shown in table 6.

Test Set-Up

UV-absorbers were mixed in the appropriate ratio (see table) in ethyl acetate/Finsolv TN (1:4) in a total UV-absorber concentration of 3 wt %. 20 µl of the solution was cast in duplo on glass plates and dried. One plate was then put in a solar sunlight simulator (Atlas Ci4000) and exposed to in total 2000 J/m². The other plate was kept in the dark and was used as reference. Hereafter the UV-absorbers were washed off with a standard amount of ethyl acetate. The concentration of inventive compound 4 was determined by HPLC while the integrated UV-absorption was calculated from the recorded UV-Vis spectrum in the range of 300-400 nm.

Results

TABLE 6

Light stability of several combinations of UV absorbing compounds

| Mixture | Weight Mix ratio | Relative Remaining Compound 4 | Relative decrease UV-absorption |
|---|---|---|---|
| Inventive compound 4:ET | 1:3 | 95% | <5% |
| Inventive compound 4:ET | 3:1 | 93% | <5% |
| Inventive compound 4: BMDBM | 1:4 | 85% | <5% |
| Inventive compound 4: BMDBM | 4:1 | 90% | <5% |
| Inventive compound 4:ET: BMDBM | 1:2:2 | 92% | <5% |
| Inventive compound 4:ET: BMDBM | 2:2:2 | 95% | <5% |
| Inventive compound 4: OMC | 1:4 | 90% | <5% |
| Inventive compound 4: OMC | 4:1 | 92% | <5% |
| Inventive compound 4: OMC:BMDBM | 2:2:2 | 88% | <5% |

The invention claimed is:

1. A UV-absorbing compound according to Formula (VII):

$$N(R^{17})_{3-n}[(CR^1{}_2)_m-N(R^{17})-CH_2R^2]_n \quad (VII)$$

wherein:
n=2-3;
m=2-12;

each $R^1$ is independently selected from the group consisting of a hydrogen atom, a $C_1$-$C_6$ alkyl group or a $C_1$-$C_6$ alkoxy group;

for m=5-12, $R^2$ is independently selected from the group consisting of a hydrogen atom, a $C_1$-$C_{20}$ alkyl group, a $C_2$-$C_{20}$ alkenyl group, a $C_2$-$C_{20}$ alkynyl group, a $C_6$-$C_{20}$ aryl group and a group of the formula —$(CR^{18}_2)_oN(R^{17})CH_2R^3$, wherein o=1-11; each $R^{18}$ is independently selected from the group consisting of a hydrogen atom, a $C_1$-$C_6$ alkyl group and a $C_1$-$C_6$ alkoxy group; and $R^3$ is independently selected from the group consisting of a hydrogen atom, a $C_1$-$C_{20}$ alkyl group, a $C_6$-$C_{20}$ aryl group and a group of the formula —$(CR^{18}_2)_pN(R^{17})CH_2R^4$, wherein p=1-11; each $R^{18}$ is as defined above; and $R^4$ is independently selected from the group consisting of a hydrogen atom, a $C_1$-$C_{20}$ alkyl group, a $C_6$-$C_{20}$ aryl group and a group of the formula —$(CR^{18}_2)_qN(R^{17})CH_2R^5$, wherein q=1-11; each $R^{18}$ is as defined above; and $R^5$ is independently selected from the group consisting of a hydrogen atom, a $C_1$-$C_{20}$ alkyl group and a $C_6$-$C_{20}$ aryl group;

for m=2-4, $R^2$ is independently selected from the group consisting of a $C_6$-$C_{20}$ alkyl group, a $C_6$-$C_{20}$ alkenyl group, a $C_6$-$C_{20}$ alkynyl group, a $C_6$-$C_{20}$ aryl group and a group of the formula —$(CR^{18}_2)_oN(R^{17})CH_2R^3$, wherein o=3-9; each $R^{18}$ is independently selected from the group consisting of a hydrogen atom, a $C_1$-$C_6$ alkyl group and a $C_1$-$C_6$ alkoxy group; and $R^3$ is independently selected from the group consisting of a hydrogen atom, a $C_1$-$C_{20}$ alkyl group, a $C_6$-$C_{20}$ aryl group and a group of the formula —$(CR^{18}_2)_pN(R^{17})CH_2R^4$, wherein p=3-9; each $R^{18}$ is as defined above; and $R^4$ is independently selected from the group consisting of a hydrogen atom, a $C_1$-$C_{20}$ alkyl group, a $C_6$-$C_{20}$ aryl group and a group of the formula —$(CR^{18}_2)_qN(R^{17})CH_2R^5$, wherein q=3-9; each $R^{18}$ is as defined above; and $R^5$ is independently selected from the group consisting of a hydrogen atom, a $C_1$-$C_{20}$ alkyl group and a $C_6$-$C_{20}$ aryl group;

wherein $R^{17}$ is independently selected from the group of substituents according to Formula (VIII):

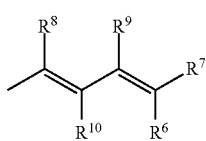

(VIII)

wherein $R^6$ and $R^7$ are independently selected from the group consisting of —CN, —C(O)OH, —C(O)O$R^{11}$, —C(O)$R^{11}$ and —S(O$_2$)$R^{11}$, wherein $R^{11}$ is a $C_6$-$C_{20}$ aryl group or a $C_1$-$C_{25}$ alkyl group, wherein the $C_1$-$C_{25}$ alkyl group is optionally substituted with one or more hetero-atom containing groups, the hetero-atom being selected from O, N, S and Si, and wherein two $R^{11}$ groups optionally form a ring structure if the $R^{11}$ groups are $C_1$-$C_{25}$ alkyl groups, said ring structure being a five to seven membered ring structure and optionally comprising a hetero-atom, said hetero-atom being selected from the group consisting of N, O and S, and/or an oxo group;

$R^8$, $R^9$ and $R^{10}$ are independently selected from the group consisting of hydrogen, a $C_1$-$C_{20}$ alkyl group, a $C_3$-$C_{20}$ alkenyl group, a $C_3$-$C_{20}$ alkynyl group, a $C_7$-$C_{20}$ aralkyl group, —CN, —O$R^{12}$, —S$R^{12}$ and —N($R^{12}R^{13}$), wherein $R^{12}$ and $R^{13}$ are independently selected from the group consisting of hydrogen, a $C_1$-$C_{20}$ alkyl group and a $C_6$-$C_{20}$ aryl group; wherein $R^8$ and $R^9$, $R^8$ and $R^{10}$ or $R^9$ and $R^{10}$ optionally form a ring structure, said ring structure optionally comprising a hetero-atom, said hetero-atom being selected from the group consisting of N, O and S, and/or an oxo group.

2. The UV-absorbing compound according to claim 1, wherein m=5-12.

3. The UV-absorbing compound according to claim 2, wherein m=6.

4. The UV-absorbing compound according to claim 1, wherein n=2.

5. The UV-absorbing compound according to claim 1, wherein $R^1$, $R^8$, $R^9$, $R^{10}$ and $R^{18}$ are hydrogen.

6. The UV-absorbing compound according to claim 1, wherein $R^6$ is S(O$_2$)$R^{11}$ and wherein $R^{11}$ is a $C_6$-$C_{20}$ aryl group.

7. The UV-absorbing compound according to claim 1, wherein $R^7$ is C(O)O$R^{11}$, wherein $R^{11}$ is a $C_1$-$C_{25}$ alkyl group.

8. The UV-absorbing compound according to claim 7, wherein $R^7$ is C(O)O$R^{11}$, wherein $R^{11}$ is a $C_1$-$C_{12}$ alkyl group.

9. The UV-absorbing compound according to claim 1, wherein $R^2$ is selected from the group consisting of a $C_6$-$C_{20}$ alkyl group, a $C_6$-$C_{20}$ alkenyl group, a $C_6$-$C_{20}$ alkynyl group and a $C_6$-$C_{20}$ aryl group.

10. The UV-absorbing compound according to claim 9, wherein $R^2$ is a $C_6$-$C_{20}$ alkyl group or a $C_6$-$C_{20}$ aryl group.

11. A method for protection of a mammal against UV radiation, wherein a composition comprising applying a UV-absorbing compound according to claim 1 to the skin of the mammal.

* * * * *